US005696280A

United States Patent [19]

Shapiro

[11] Patent Number: 5,696,280
[45] Date of Patent: Dec. 9, 1997

[54] HYDROCYANATION OF DIOLEFINS AND ISOMERIZATION OF NONCONJUGATED 2-ALKYL-3-MONOALKENENITRILES

[75] Inventor: Rafael Shapiro, Wilmington, Del.

[73] Assignee: E. I. Du Pont de Nemours and Company, Wilmington, Del.

[21] Appl. No.: 729,457

[22] Filed: Oct. 11, 1996

Related U.S. Application Data

[60] Division of Ser. No. 563,718, Nov. 28, 1995, which is a continuation-in-part of Ser. No. 379,429, Jan. 27, 1995, abandoned.

[51] Int. Cl.$^6$ .................................................. C07F 9/14
[52] U.S. Cl. .................................. 558/140; 558/144
[58] Field of Search .............................. 558/140, 144

[56] References Cited

U.S. PATENT DOCUMENTS

| | | | |
|---|---|---|---|
| 2,934,564 | 4/1960 | Burg et al. | 260/543 |
| 3,496,210 | 2/1970 | Drinkard, Jr. et al. | 260/465 |
| 3,496,215 | 2/1970 | Drinkard, Jr. et al. | 260/465.8 |
| 3,496,217 | 2/1970 | Drinkard, Jr. et al. | 260/465 |
| 3,496,218 | 2/1970 | Drinkard, Jr. | 260/465.8 |
| 3,536,748 | 10/1970 | Drinkard, Jr. et al. | 260/465.9 |
| 3,547,942 | 12/1970 | Godefroi et al. | 260/309 |
| 3,574,701 | 4/1971 | Kominami et al. | 260/465.3 |
| 3,578,695 | 5/1971 | Milberger et al. | 260/465.3 |
| 3,584,029 | 6/1971 | Kominami et al. | 260/465.3 |
| 3,631,191 | 12/1971 | Kane et al. | 260/439 |
| 3,655,723 | 4/1972 | Drinkard, Jr. | 260/465.3 |
| 3,676,481 | 7/1972 | Chia | 260/465.9 |
| 3,739,011 | 6/1973 | Drinkard, Jr. | 558/355 |
| 3,766,231 | 10/1973 | Gosser et al. | 260/439 R |
| 3,766,237 | 10/1973 | Chia et al. | 260/465.3 |
| 3,773,809 | 11/1973 | Walter | 260/465.8 |
| 3,775,461 | 11/1973 | Drinkard et al. | 260/465.3 |
| 3,798,256 | 3/1974 | King et al. | 558/338 |
| 3,846,461 | 11/1974 | Shook, Jr. | 260/439 R |
| 3,847,959 | 11/1974 | Shook, Jr. et al. | 260/439 R |
| 3,852,325 | 12/1974 | King | 558/355 |
| 3,852,328 | 12/1974 | Chia et al. | 558/355 |
| 3,852,329 | 12/1974 | Tomlinson | 558/355 |
| 3,853,948 | 12/1974 | Drinkard, Jr. et al. | 558/355 |
| 3,865,864 | 2/1975 | Nakajima et al. | 260/465.3 |
| 3,869,500 | 3/1975 | Kominami et al. | 260/465.3 |
| 3,903,120 | 9/1975 | Shook, Jr. et al. | 260/439 R |
| 3,925,445 | 12/1975 | King et al. | 558/338 |
| 4,298,546 | 11/1981 | McGill | 558/355 |
| 4,371,474 | 2/1983 | Rapoport | 558/338 |
| 4,599,206 | 7/1986 | Billig et al. | 558/85 |
| 4,668,651 | 5/1987 | Billig et al. | 502/158 |
| 4,705,881 | 11/1987 | Rapoport | 558/338 |
| 4,714,773 | 12/1987 | Rapoport | 558/338 |
| 4,717,775 | 1/1988 | Billig et al. | 568/454 |
| 4,769,498 | 9/1988 | Billig et al. | 568/454 |
| 4,774,353 | 9/1988 | Hall et al. | 558/335 |
| 4,783,546 | 11/1988 | Burke et al. | 558/355 |
| 4,874,884 | 10/1989 | McKinney et al. | 558/338 |
| 5,202,297 | 4/1993 | Lorz et al. | 502/106 |
| 5,235,113 | 8/1993 | Sato | 568/454 |
| 5,288,918 | 2/1994 | Maher et al. | 568/454 |
| 5,312,957 | 5/1994 | Casalnuovo et al. | 558/410 |
| 5,440,067 | 8/1995 | Druliner | 558/355 |
| 5,449,807 | 9/1995 | Druliner | 568/454 |
| 5,512,695 | 4/1996 | Kreutzer et al. | 558/338 |
| 5,512,696 | 4/1996 | Kreutzer et al. | 558/338 |
| 5,543,536 | 8/1996 | Tam | 556/13 |

FOREIGN PATENT DOCUMENTS

| | | | |
|---|---|---|---|
| A-0 005 500 | 11/1979 | European Pat. Off. | C07F 9/24 |
| 0 518 241 | 12/1992 | European Pat. Off. | C07C 45/50 |
| 6916495 | 5/1971 | Netherlands | C07C 121/00 |
| 1 417 554 | 12/1975 | United Kingdom | C07F 9/02 |
| WO 85/03702 | 8/1985 | WIPO | C07C 45/50 |
| WO 93/03839 | 3/1993 | WIPO | B01J 31/24 |
| WO 95/14659 | 6/1995 | WIPO | C07C 253/10 |

OTHER PUBLICATIONS

Cuny, G.D. et al., "Practical High-Yield, Regioselective, Rhodium-Catalyzed Hydroformylation of Functionalized α-Olefins", *J. Am. Chem. Soc.*, 115, 2066–2068 (1993).

Burgstahler, A.W. et al., "Improved Modification of the Rosenmund Reduction", *Synthesis*, 767–768 (1976).

Tolman, C.A. et al., "Homogeneous Nickel-Catalyzed Olefin Hydrocyanation", *Advances in Catalysis*, 33 1–46 (1985).

Baker, M.J. et al., "Chelating Diphosphite Complexes of Nickel(0) and Platinum(0): Their Remarkable Stability and Hydrocyanation Activity", *J. Chem. Soc. Chem. Commun.*, pp. 803–804 (1991).

Baker, M.J. et al., "Chiral Aryl Diphosphites: A New Class of Ligands for Hydrocyanation Catalysis", *J. Chem. Soc., Chem. Communi.*, 1292–1293 (1991).

Seidel, W.C. et al., "Ethylene[bis(tri-o-tolyl phosphite)] nickel(0)", *Inorganic Chemistry*, 9(10), 2354–2357 (1970).

Kurokawa, H. et al., "Skeletal Rearrangement of Unsaturated Nitriles over Solid-Base Catalysts", *J. of Catalysis*, 141, 94–101 (1993).

Pastor, S.D. et al., "Conformation of Eight-Membered Dioxathiasilocin Heterocycles in Solution", *Phosphorus and Sulfur*, 32, 105–111 (1987).

Yamada, F. et al., "Substituted Bisphenols as Antioxidants for Autoxidation of Tetralin", *Bull Chem. Soc. Japan*, 62, 3603–3608 (1989).

G. Markl et al., Zur Chemie des Cyclooctatetraenyldilithiums, *Journal of Organometallic Chemistry*, 273, 1–29, 1984.

Zh. M. Ivanova, Phosphoramidous Difluorides, *J. Gen. Chem. USSR*, 35, 165–7, 1965.

J. Heinicke et al., 1,3–Carbanionische Umlagerungen, Synthese von Bis(o–hydroxyaryl)–Phosphorverbindungen, *Phosphorus, Sulfur Silicon Relat. Elem.*, 44, 209–16, 1989.

Scherer, O.J. et al., Z. Naturforsch, 1972, 27B, 1429, Nov. 1972.

*Primary Examiner*—José G. Dees
*Assistant Examiner*—Laura L. Stockton

[57] ABSTRACT

Improved liquid phase process useful in the hydrocyanation of diolefinic compounds to produce nonconjugated acyclic nitriles and to the liquid phase process of isomerization of the nitriles to 3- and/or 4-monoalkene linear nitriles. The improvement involves conducting the process in the presence of zero-valent nickel and a multidentate phosphite ligand. The invention also provides a novel method of making phosphorochloridite.

2 Claims, No Drawings

HYDROCYANATION OF DIOLEFINS AND ISOMERIZATION OF NONCONJUGATED 2-ALKYL-3-MONOALKENENITRILES

CROSS-REFERENCE TO RELATED APPLICATION

This is a division of application Ser. No. 08/563,718, filed Nov. 28, 1995 which, is a continuation-in-part application of application Ser. No. 08/379,429 filed Jan. 27, 1995, now abandoned.

FIELD OF THE INVENTION

This invention generally relates to an improved liquid phase process useful in the hydrocyanation of diolefinic compounds to produce nonconjugated acyclic nitriles and to a liquid phase process of isomerization of said nitriles to 3- and/or 4-monoalkene linear nitriles. The improvement resides in conducting the process in the presence of zero-valent nickel and a multidentate phosphite ligand.

BACKGROUND OF THE INVENTION

Catalytic hydrocyanation systems, particularly pertaining to the hydrocyanation of olefins, are known in the art. For example, liquid phase systems useful for the hydrocyanation of butadiene to form pentenenitriles (PN) are known in the art. For example, Drinkard, U.S. Pat. No. 3,496,215, discloses the hydrocyanation of butadiene using monodentate nickel phosphite catalysts. As used in this patent, and as will be used herein, the term "pentenenitrile" is intended to mean cyanobutene. Likewise, "butenenitrile" means cyanopropene. Bidentate phosphite ligands complexed to zero-valent nickel and platinum are known to be useful in the liquid phase hydrocyanation of butadiene, as described by Baker et al., *J. Chem. Soc.*, Chem. Commun., 1991, pages 803–804.

The pentenenitriles so formed are subjected to further hydrocyanation and/or isomerization to form adiponitrile (ADN), a commercially important material in the manufacture of nylon. For example, Drinkard, U.S. Pat. No. 3,536,748, discloses the liquid phase isomerization of 2-methyl-3-butenenitrile in the presence of a zero valent nickel complex and Chia, U.S. Pat. No. 3,676,481, discloses an improvement additionally utilizing tri(hydrocarbyl)boron promoters.

The hydrocyanation of activated olefins such as conjugated olefins (e.g., butadiene and styrene) and strained olefins (e.g., norbornene) proceeds without the use of a Lewis acid promoter, while hydrocyanation of unactivated olefins such as 1-octene and 3-pentenenitrile normally require the use of a Lewis acid promoter. Teachings regarding the use of a promoter in the hydrocyanation reaction appear, for example, in U.S. Pat. No. 3,496,217.

Certain multidentate phosphite ligands useful in the present invention for the hydrocyanation of diolefins have been used for the hydrocyanation of monoolefins. Commonly assigned, copending application Ser. No. 08/424,351, fled Apr. 26, 1995, and copending application U.S. Ser. No. 08/505,137, filed Jul. 21, 1995, disclose bidentate phosphite ligands preferably used in combination with a Lewis acid promotor to hydrocyanate monoolefins.

The present invention provides for an improved process for the hydrocyanation of diolefinic compounds, such as butadiene, and isomerization of nonconjugated acyclic nitriles without the need for Lewis acid promoters utilizing zero-valent nickel and a multidentate phosphite ligand. Other objects and advantages of the present invention will become apparent to those skilled in the art upon reference to the detailed description of the invention which hereinafter follows.

SUMMARY OF THE INVENTION

The present invention provides an improved process for the liquid phase hydrocyanation of diolefinic compounds and isomerization of the resulting nonconjugated acyclic nitriles comprising, reacting an acyclic aliphatic diolefinic compound, preferably butadiene, with a source of HCN, wherein the improvement comprises conducting the hydrocyanation and/or isomerzation in the presence of a catalyst precursor composition comprising zero-valent nickel and at least one multidentate phosphite ligand selected from the group consisting of compounds represented by Formulas I, II, III, IV, V, VI, VII, VIII, IX, X, XI, XII, XIII, XIV, and XV as set forth below:

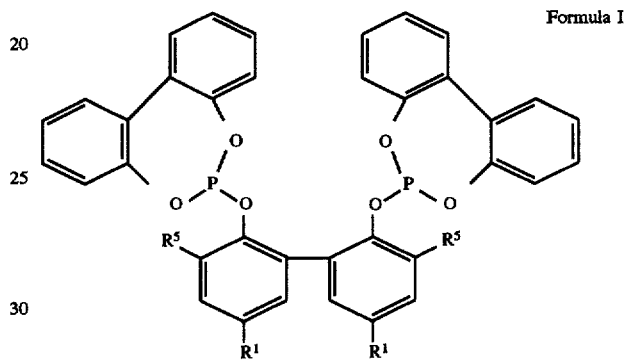

Formula I wherein
each $R^1$ is independently a branched or straight chain alkyl of up to 12 carbon atoms, or $OR^4$ wherein $R^4$ is $C_1$ to $C_{12}$ alkyl;
each $R^5$ is independently a tertiary substituted hydrocarbon of up to 12 carbon atoms;

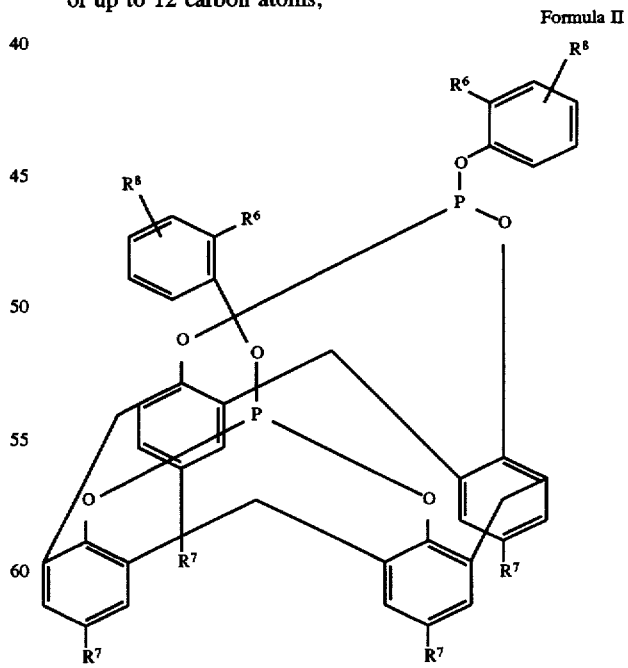

Formula II wherein
each $R^6$ and $R^7$ is independently a tertiary substituted hydrocarbon of up to 12 carbon atoms; and each R⁸ is independently H or a branched or straight chain alkyl of up to 12 carbon atoms, or OR⁴ wherein R⁴ is C₁ to C₁₂ alkyl;

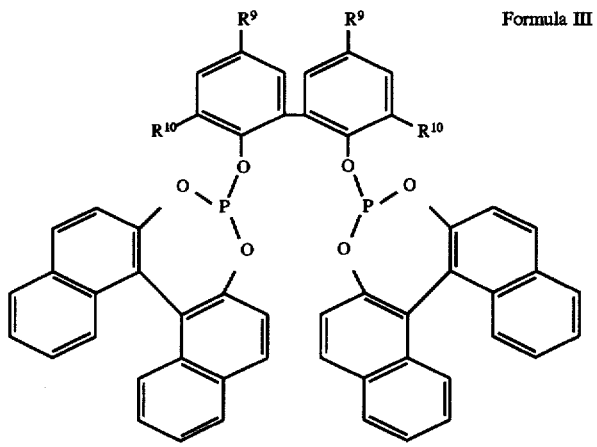

Formula III wherein each R⁹ is independently H or a branched or straight chain alkyl of up to 12 carbon atoms, or OR⁴ wherein R⁴ is C₁ to C₁₂ alkyl; and each R¹⁰ is independently a tertiary substituted hydrocarbon of up to 12 carbon atoms;

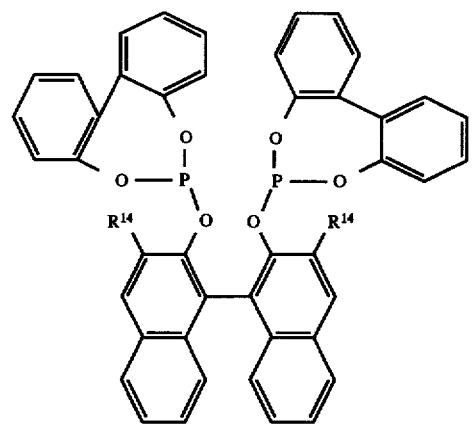

Formula IV wherein each R¹⁴ is independently a tertiary substituted hydrocarbon of up to 12 carbon atoms or Si(R¹¹)₃ where R¹¹ is independently a branched or straight chain alkyl of up to 12 carbon atoms or phenyl or R¹⁴ can be CO₂R³" wherein R³" is a secondary alkyl of up to 6 carbon atoms;

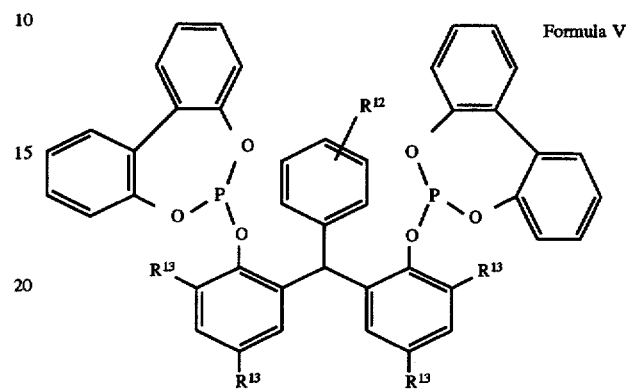

Formula V wherein

R¹² is H or a branched or straight chain alkyl of up to 12 carbon atoms; and each R¹³ is independently a branched or straight chain alkyl of up to 12 carbon atoms;

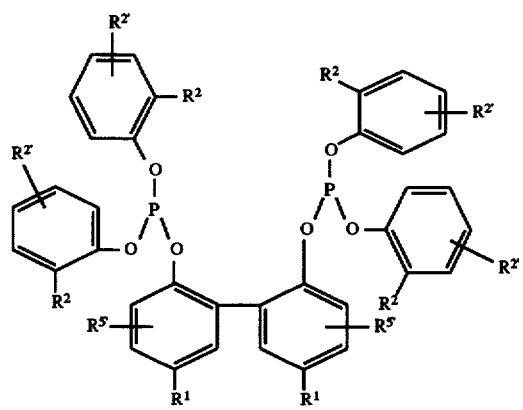

Formula VI

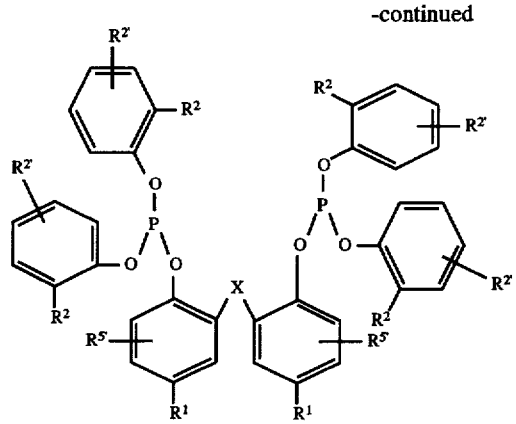
Formula VII
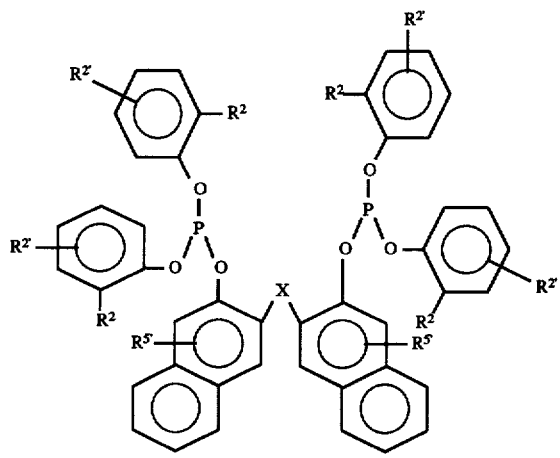
Formula VIII
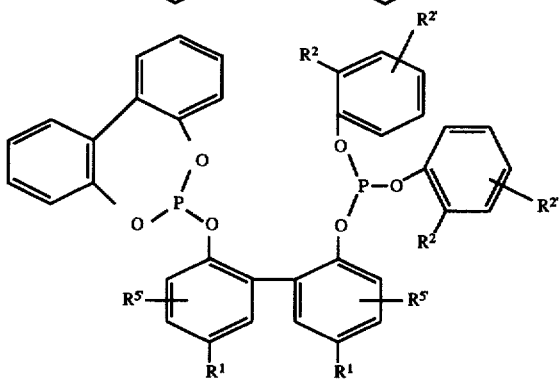
Formula VIX
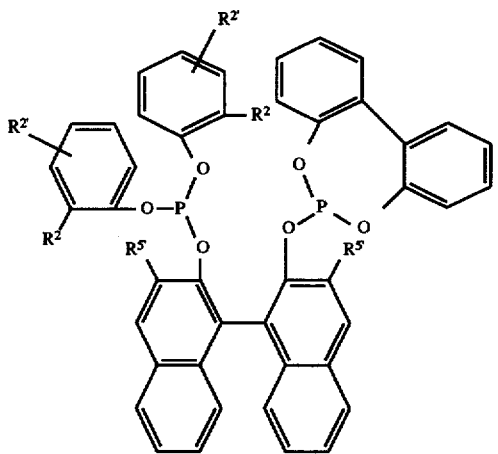
Formula X Formula XI
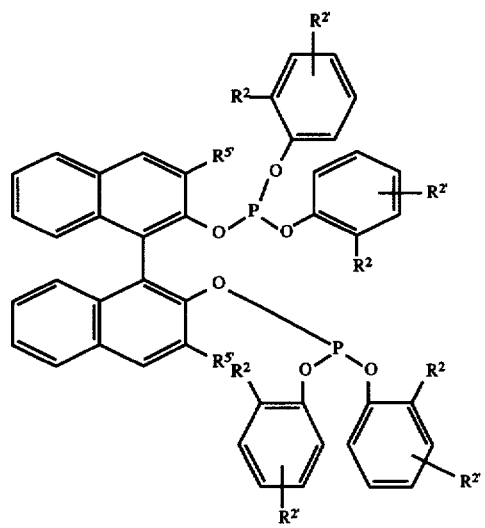
Formula XII
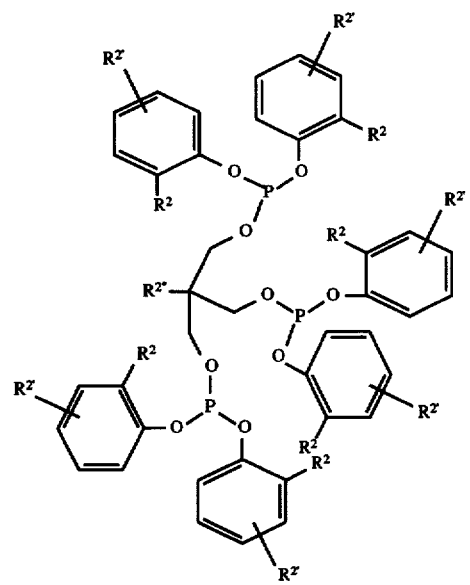
Formula XIII
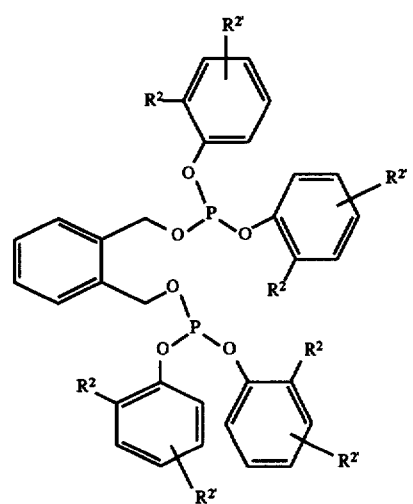

-continued

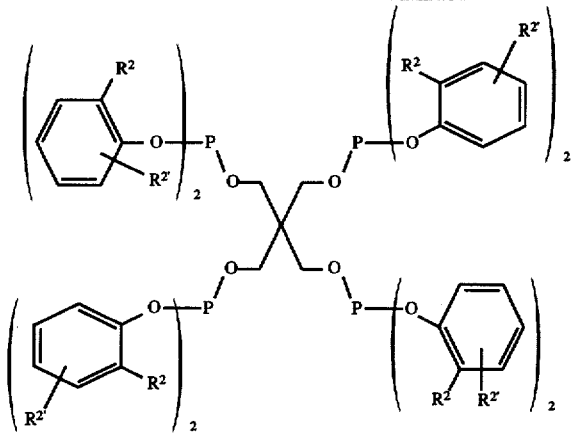

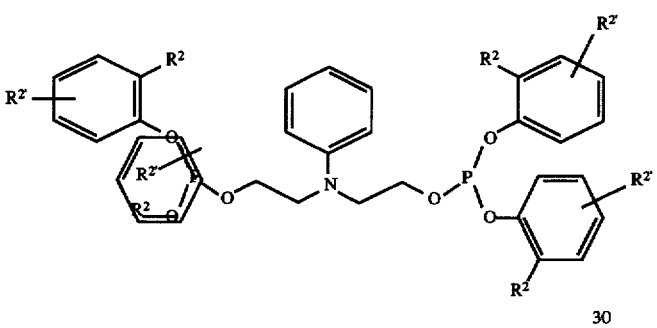

wherein in Formulas VI through XV each $R^1$ is independently, H, halogen, a $C_1$ to $C_{12}$ alkyl, or $OR^3$ wherein $R^3$ is a $C_1$ to $C_{12}$ alkyl;

each $R^2$ is independently a secondary or tertiary hydrocarbyl of 3 to 12 carbon atoms, or $OR^{4''}$ wherein $R^{4''}$ is $C_1$ to $C_6$ alkyl or benzyl; or a cyclic group of the formula

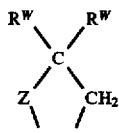

forming a five membered ring attached to the phenyl ring, wherein $R^w$ is H or $CH_3$ and Z is —O— or —$CH_2$—;

each $R^{2'}$ is independently H or a primary, secondary or tertiary hydrocarbyl of 1 to 12 carbon atoms at either the meta or para position to the oxygen; or CN, $CO_2R^{4''}$ or $OR^{4''}$ wherein $R^{4''}$ is a $C_1$ to $C_6$ alkyl at either the meta or para position to the oxygen of the phenoxy ring;

each $R^{5'}$ is independently H or a primary or secondary hydrocarbyl of 1 to 3 carbon atoms; for Formulas VI and IX, $R^{5'}$ can also be $OR^{4''}$ wherein $R^{4''}$ is a $C_1$ to $C_6$ alkyl; for Formulas X and XI, $R^{5'}$ can also be $CO_2R^{4''}$ wherein $R^{4''}$ is a $C_1$ to $C_6$ alkyl; and each X is independently O or $CH(R^{4'})$, wherein $R^{4'}$ is H, a substituted phenyl, or a $C_1$ to $C_{12}$ alkyl;

and wherein said reaction is carded out to ultimately produce 3 and/or 4-monoalkene linear nitriles.

The present invention provides an improved process for the liquid phase hydrocyanation of diolefinic compounds, reacting an acyclic aliphatic diolefinic compound, preferably butadiene, with a source of HCN, wherein the improvement comprises conducting the hydrocyanation in the presence of a catalyst precursor composition comprising zero-valent nickel and at least one multidentate phosphite ligand selected from the group consisting of compounds represented by Formulas I, II, III, IV, V, VI, VII, VIII, IX, X, XI, XII, XIII, XIV, and XV as set forth below:

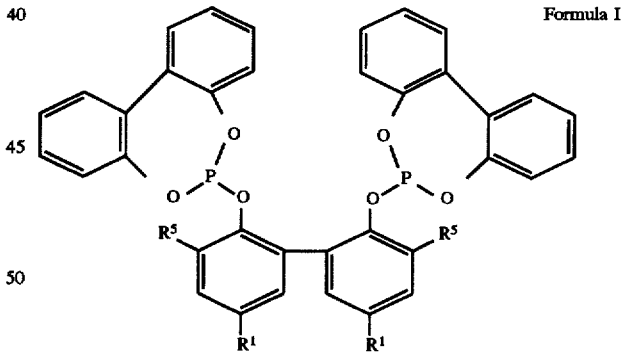

wherein each $R^1$ is independently a branched or straight chain alkyl of up to 12 carbon atoms, or $OR^4$ wherein $R^4$ is $C_1$ to $C_{12}$ alkyl;

each $R^5$ is independently a branched or straight chain alkyl of up to 12 carbon atoms or $OR^{4''}$ wherein $R^{4''}$ is $C_1$ to $C_6$ alkyl;

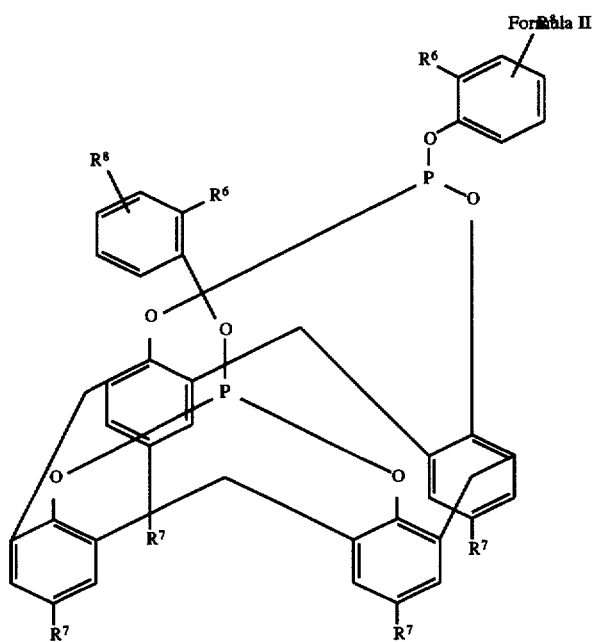

wherein
each $R^6$ and $R^7$ is independently a tertiary substituted hydrocarbon of up to 12 carbon atoms; and
each $R^8$ is independently H or a branched or straight chain alkyl of up to 12 carbon atoms, or $OR^4$ wherein $R^4$ is $C_1$ to $C_{12}$ alkyl;

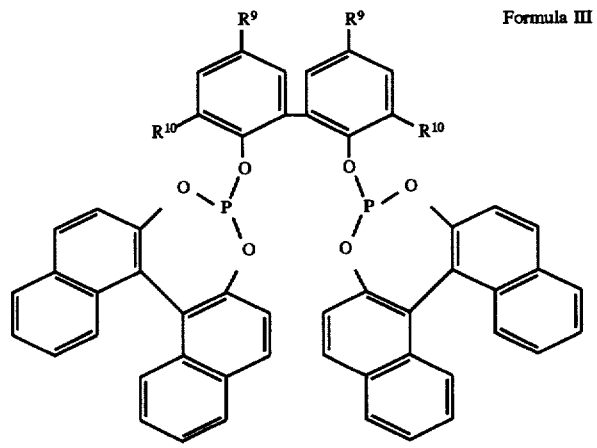

wherein each $R^9$ is independently H or a branched or straight chain alkyl of up to 12 carbon atoms, or $OR^4$ wherein $R^4$ is $C_1$ to $C_{12}$ alkyl; and
each $R^{10}$ is independently a branched or straight chain alkyl of up to 12 carbon atoms or $OR^{4''}$ wherein $R^{4''}$ is $C_1$ to $C_6$ alkyl;

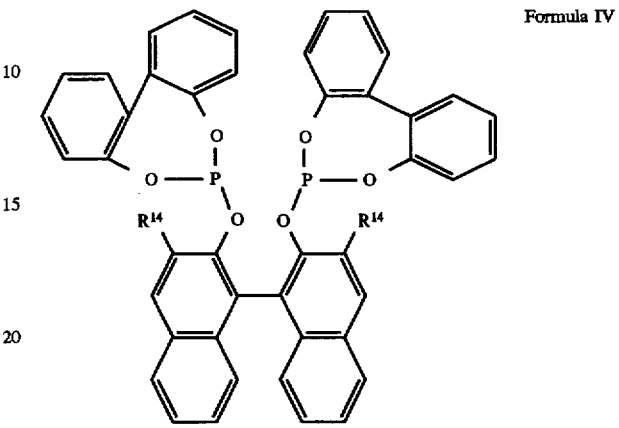

wherein
each $R^{14}$ is independently a branched or straight chain alkyl of up to 12 carbon atoms or $Si(R^{11})_3$ where $R^{11}$ is independently a branched or straight chain alkyl of up to 12 carbon atoms or phenyl or $CO_2R^{4''}$ wherein $R^{4''}$ is $C_1$ to $C_6$ alkyl;

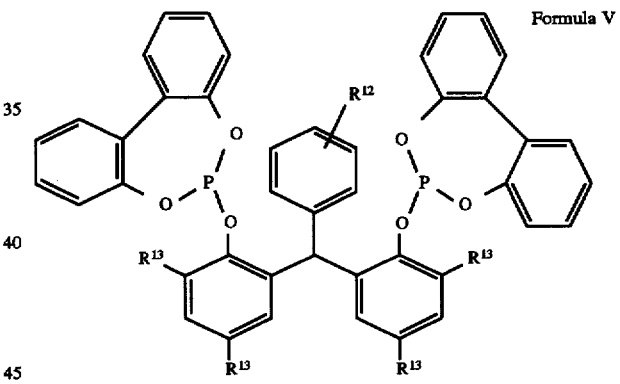

wherein
$R^{12}$ is H or a branched or straight chain alkyl of up to 12 carbon atoms; and
each $R^{13}$ is independently a branched or straight chain alkyl of up to 12 carbon atoms;

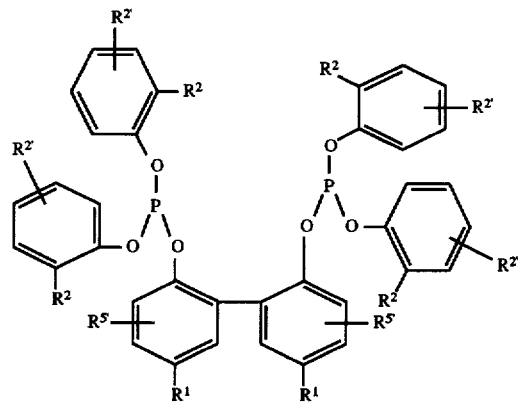
Formula VI
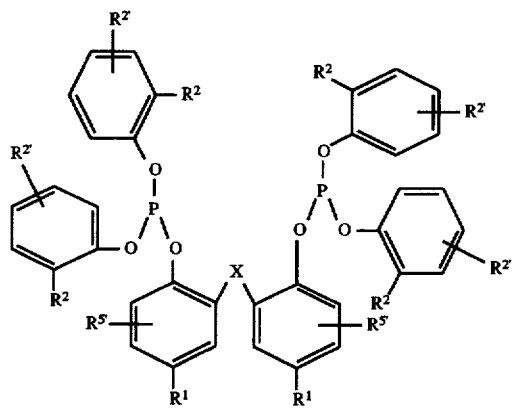
Formula VII
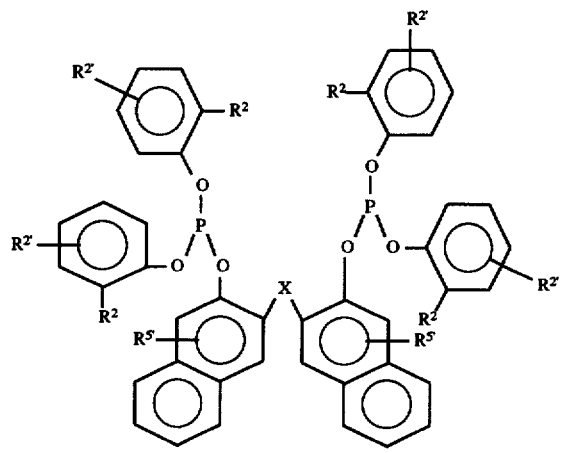
Formula VIII
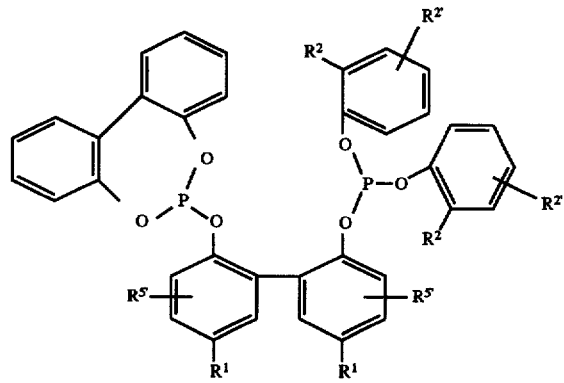
Formula VIX

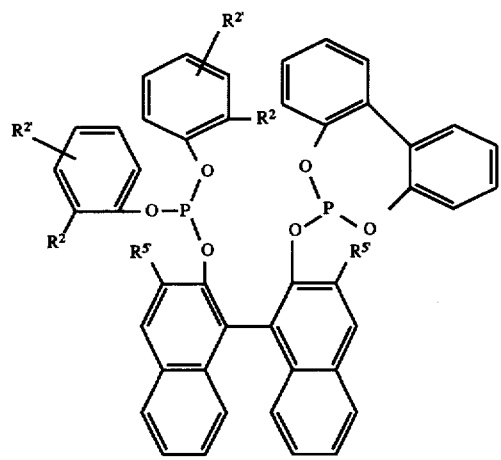
Formula X
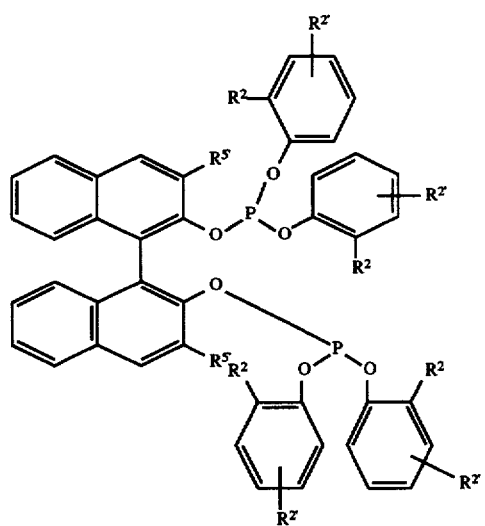
Formula XI
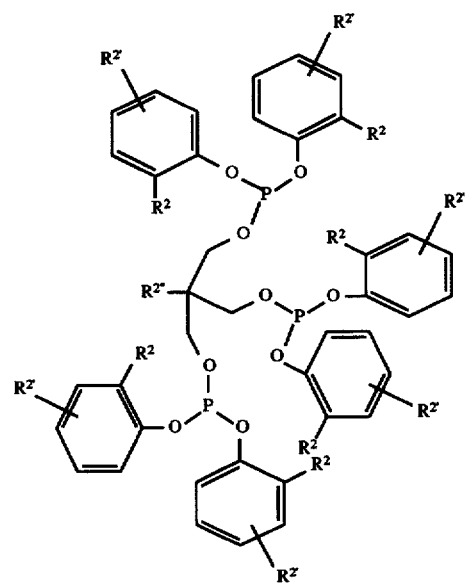
Formula XII

-continued

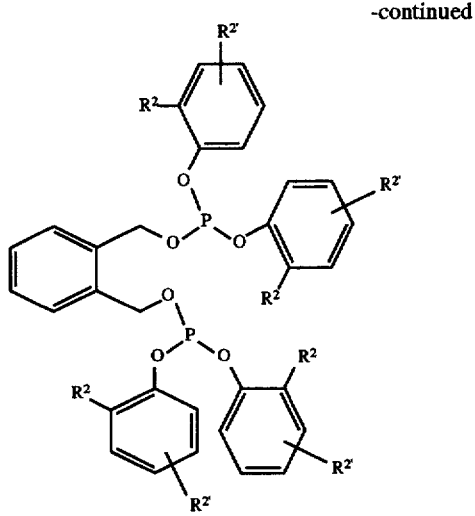

Formula XIII

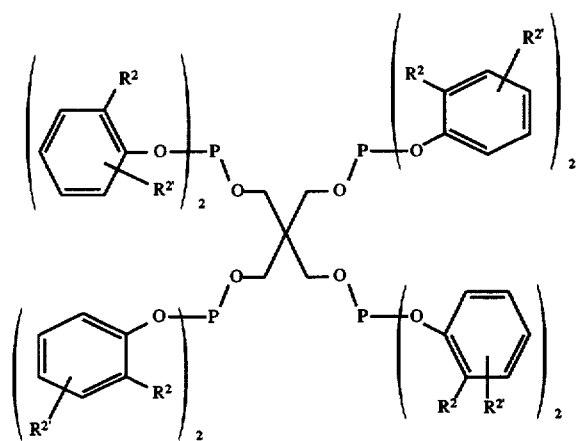

Formula XIV

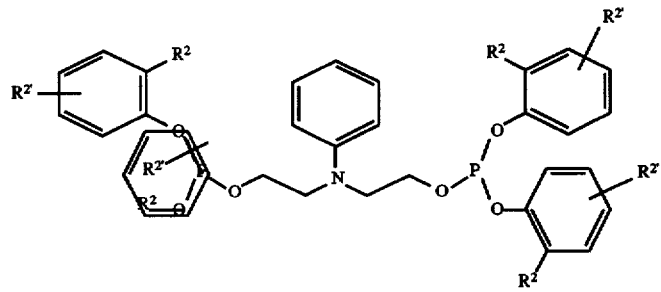

Formula XV wherein in Formulas VI through XV each $R^1$ is independently, H, halogen, a $C_1$ to $C_{12}$ alkyl, or $OR^3$ wherein $R^3$ is a $C_1$ to $C_{12}$ alkyl;

each $R^2$ is independently a secondary or tertiary hydrocarbyl of 3 to 12 carbon atoms, or $OR^{4''}$ wherein $R^{4''}$ is $C_1$ to $C_6$ alkyl or benzyl; or a cyclic group of the formula

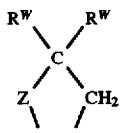

forming a five membered ring attached to the phenyl ring, wherein $R^w$ is H or $CH_3$ and Z is —O— or —$CH_2$—;

each $R^{2'}$ is independently H or a primary, secondary or tertiary hydrocarbyl of 1 to 12 carbon atoms at either the mete or pare position to the oxygen; or CN, $CO_2R^{4''}$ or $OR4''$ wherein $R^{4''}$ is a $C_1$ to $C_6$ alkyl at either the meta or para position to the oxygen of the phenoxy ring;

each $R^{5'}$ is independently H or a primary or secondary hydrocarbyl of 1 to 3 carbon atoms; for Formulas VI and IX, $R^{5'}$ can also be $OR^{4''}$ wherein $R^{4''}$ is a $C_1$ to $C_6$ alkyl; for Formulas X and XI, $R^{5'}$ can also be $CO_2R^{4''}$ wherein $R^{4''}$ is a $C_1$ to $C_6$ alkyl; and each X is independently O or $CH(R^{4'})$, wherein $R^{4'}$ is H, a substituted phenyl, or a $C_1$ to $C_{12}$ alkyl;

and wherein said reaction is carried out to ultimately produce 3 and/or 4-monoalkene linear nitriles and 2-alkyl-3-monoalkenenitriles.

As used herein, the terms "secondary" and "tertiary" refer to the carbon atom bonded to an aromatic ring.

The reactions are most conveniently performed continuously from hydrocyanation of the starting diolefin to the final 3- and/or 4-monoalkene linear nitriles. However, the processes can be conducted stepwise, i.e., the nonconjugated acyclic nitriles resulting from the hydrocyanation can be isolated per se, prior to isomerization. Furthermore, nonconjugated acyclic nitriles prepared by any method can be used as starting materials for the isomerization in accordance with this invention.

The invention also provides for certain multidentate phosphite ligands and catalyst precursor compositions made therefrom useful in these processes as well as a novel method of making phosphorochloridite.

In particular, the method of making phosphorochloridite comprises contacting a compound of the formula $N(R^{18})_2P(OR^{19})_2$, wherein $R^{18}$ is alkyl and $R^{19}$ is substituted aryl, with gaseous hydrogen chloride (HCl) to produce $HN(R^{18})_2 \cdot HCl$ and $(R^{19}O)_2PCl$. Preferably, the reaction is run without excess HCl, or if excess HCl is present, the HCl is removed quickly after the reaction is complete to prevent decomposition of the $(R^{19}O)_2PCl$ product.

A method is also provided for producing N,N-dialkyldiarylphosphoramidite comprising contacting one equivalent of $PCl_3$ in an inert solvent, such as heptane or toluene, with one equivalent of a secondary amine, such as diisopropylamine, and at least one equivalent of a tertiary amine, such as triethylamine, preferably in the range of about 5° to about 35° C., and subsequently adding about 1.9 equivalents of a substituted phenol and about 2.1 equivalents of a tertiary amine, such as triethylamine, preferably in the presence of a nucleophilic catalyst such as 4-dimethylaminopyridine, and allowing the components to react at about 25° to about 90° C. Practice of the above method eliminates the need to isolate the intermediate (R 18)2NPCl2.

DETAILED DESCRIPTION OF THE PREFERRED EMBODIMENTS.

The catalyst precursor compositions useful in the processes of this invention are comprised of a multidentate phosphite ligand and zero-valent nickel. The preferred ligand of the invention (for hydrocyanation of diolefinic compounds and the subsequent and/or independent isomerization of nonconjugated acyclic nitriles to 3- and/or 4-monoalkene linear nitriles) is described below by Formula I, wherein each R 1 is independently a branched or straight chain alkyl containing up to 12 carbon atoms, or $OR^4$ wherein $R^4$ is a $C_1$ to C12 alkyl. $R^4$ can be primary, secondary or tertiary; examples include methyl, ethyl, isopropyl and t-butyl. Each $R^1$ may be the same or different. In a more preferred ligand, both R 1 groups are $OR^4$ wherein $R^4$ is methyl. $R^5$ is a tertiary substituted hydrocarbyl group containing up to 12 single bond carbon atoms. Most preferably, each R 1 is $OCH_3$ and each $R^5$ is t-butyl. For the per se hydrocyanation of diolefinic compounds to nonconjugated acyclic nitriles, $R^5$ is expanded to include secondary and primary alkyls of up to 12 carbon atoms and $OR^{4"}$ wherein $R^{4"}$ is $C_1$ to $C_6$ alkyl.

The catalyst composition is referred to as a "precursor" only to indicate in all likelihood, during the hydrocyanation reaction the structure of the active catalyst composition may in fact be complexed to an olefin.

These ligands may be prepared by a variety of methods known in the art, for example, see descriptions in WO 93,03839, U.S. Pat. No. 4,769,498; U.S. Pat. No. 4,688,651, *J. Amer. Chem. Soc.*, 1993, 115, 2066. The reaction of 2,2'-biphenol with phosphorus trichloride gives 1,1'-biphenyl-2,2'-diyl phosphorochloridite. The reaction of this chloridite with 2,2'-dihydroxy-3,3'-di-t-butyl-5,5'-dimethoxy- 1,1'-biphenyl in the presence of triethylamine gives the most preferred ligand wherein $R^1$ is methoxyl.

The phosphorochloridite may be prepared by a variety of methods known in the art, for example, see descriptions in Polymer, 1992, 33, 161; *Inorganic Syntheses*, 1966, 8, 68; U.S. Pat. No. 5,210,260; *Z. Anorg. Allg. Chem.*, 1986, 535, 221. With bulky ortho-substituted phenols (e.g., 2-t-butylphenol), phosphorochloridites can be prepared in situ from $PCl_3$ and the phenol. With less bulky groups (e.g., 2,3-dimethoxyphenol), purification by high vacuum distillation is typically necessary. High vacuum distillation is difficult for large scale operations.

An improved process for preparing the phosphorochloridite comprises treatment of N,N-dialkyl diarylphosphoramidite with HCl. $ClP(OMe)_2$ has been prepared in this manner, see *Z. Naturforsch*, 1972, 27B, 1429; however, phosphorochloridites derived from substituted phenols have not been previously prepared using this procedure. N,N-dialkyl diarylphosphoramidites may be prepared by methods known in the art, for example, see descriptions in *Tetrahedron Letters*, 1993, 34, 6451 and *Aust. J. Chem*, 1991, 233.

Other multidentate phosphite ligands of the invention are described above by Formulas II through XV. While these ligands are not as preferred as Formula I, they nevertheless are considered useful ligands of the present invention. Presently, while Formula I is most preferred, Formulas VII and XI are more preferred than the other remaining ligands.

The zero-valent nickel can be prepared or generated according to techniques known in the art (U.S. Pat. Nos. 3,496,217; 3,631,191; 3,846,461; 3,847,959; and 3,903,120 which are incorporated herein by reference). Zero-valent nickel compounds that contain ligands which can be displaced by the organophosphorus ligand are a preferred source of zero-valent nickel. Two such preferred zero-valent nickel compounds are $Ni(COD)_2$ (COD is 1,5-cyclooctadiene) and $Ni(P(O—o—C_6H_4CH_3)_3)_2(C_2H_4)$, both of which are known in the art. Alternatively, divalent nickel compounds may be combined with a reducing agent, and are then able to serve as suitable sources of zero-valent nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120, is also a suitable source of zero-valent nickel.

The actual catalyst precursor is a complex of zero-valent nickel with the multidentate ligand, which is formed when those two materials are combined. An effective catalyst requires at least two moles of P atoms for one gram-atom of zero-valent nickel.

The diolefinic compounds reactants used in this invention include primarily conjugated diolefins containing from 4 to 10 carbon atoms; for example, 1,3-butadiene and cis and trans-2,4-hexadienes. Butadiene is especially preferred by reason of its commercial importance in the production of adiponitrile. Other suitable diolefinic compounds include diolefinic compounds substituted with groups which do not deactivate the catalyst, for example, cis and trans-1,3-pentadienes.

The following Formulas XVI and XVII illustrate suitable representative starting diolefinic compounds; and Formulas XVIII, XIX, and XX represent the products obtained from 1,3-butadiene and HCN.

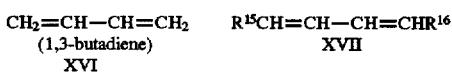

(1,3-butadiene)  
XVI

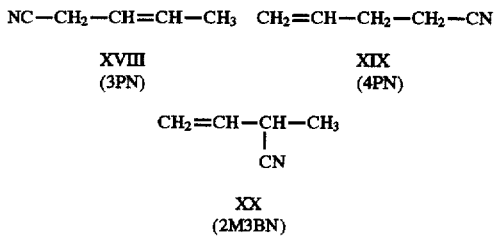

wherein each one of $R^{15}$ and $R^{16}$, independently, is H or a $C_1$ to $C_3$ alkyl.

NC—CH$_2$—CH=CH—CH$_3$     CH$_2$=CH—CH$_2$—CH$_2$—CN

XVIII                XIX  
(3PN)                (4PN)

CH$_2$=CH—CH—CH$_3$  
             |  
             CN

XX  
(2M3BN)

It will be recognized that Compound XVI is a special case of Formula XVII, where each one of $R^{15}$ and $R^{16}$ is hydrogen.

In the practice of the hydrocyanation of the diolefin in accordance with the present invention, the following description applies.

The hydrocyanation reaction can be carried out with or without a solvent. The solvent should be a liquid at the reaction temperature and inert towards the unsaturated compound and the catalyst. Generally, such solvents are hydrocarbons such as benzene, xylene, or nitriles such as acetonitrile, benzonitrile, or adiponitrile.

The exact temperature used is dependent, to a certain extent, on the particular catalyst being used, the particular unsaturated compound being used and the desired rate. Generally, temperatures of from −25° C. to 200° C., can be used with from 0° C. to 150° C., being the preferred range.

The reaction may be carried out by charging a reactor with all of the reactants or preferably the reactor is charged with the catalyst or catalyst components, the unsaturated compound and whatever solvent is to be used and the hydrogen cyanide gas is swept over the surface of the reaction mixture or bubbled through said reaction mixture. If desired, when using a gaseous unsaturated organic compound, the hydrogen cyanide and the unsaturated organic compound may be fed together into the reaction medium. The molar ratio of HCN to catalyst generally is varied from about 10:1 to 100,000:1, preferably 100:1 to 5,000:1, for a batch operation. In a continuous operation, such as when using a fixed bed catalyst type of operation, a higher proportion of catalyst may be used such as 5:1 to 100,000:1, preferably 100:1 to 5,000:1, HCN to catalyst.

Preferably, the reaction mixture is agitated, such as by stirring or shaking.

The cyanated product can be recovered by conventional techniques such as crystallization of the product from solution or by distillation.

One can either isolate the 2-alkyl3-monoalkenenitriles produced by the hydrocyanation of the diolefin or proceed continuously with the isomerization under similar reaction conditions.

The 2-alkyl-3-monoalkenenitriles used as the starting materials in the isomerization of this invention can result from the hydrocyanation of diolefin described above or can come from any other available source. The olefinic double bond in the 2-alkyl-3-monoalkenenitriles used as the starting materials in the isomerization of this invention cannot be conjugated to the triple bond of the cyano group. Suitable starting 2-alkyl-3-monoalkenenitriles can also carry groups which do not attack the catalyst, for example, another cyano group. Preferably, the starting 2-alkyl-3-monoalkenenitriles contain from 5 to 8 carbon atoms, excluding any additional substitution. 2-Methyl-3-butenenitrile is especially important in the production of adiponitrile. Other representative nitriles include 2-ethyl-3-butenenitrile and 2-propyl-3-butenenitrile.

The following Formulas XXI and XXII illustrate suitable representative starting 2-alkyl-3-monoalkenenitriles. When the starting nitrile is 2-methyl-3-butenenitrile, the isomerization products are those shown in Formulas XXIII and XXIV.

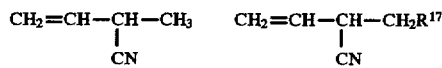

Formula XXI          Formula XXII wherein  
$R^{17}$ is H or a $C_1$ to $C_3$ alkyl.

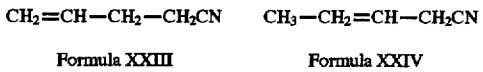

Formula XXIII         Formula XXIV

It will be recognized that Formula XXI is a special case of Formula XXII, where $R^{17}$ is hydrogen.

The isomerization process of this invention can be carried out, for example, at atmospheric pressure and at any temperature in the range of 10°–200° C., preferably in the range 60°–150° C. The pressure is not critical, however, and can be above or below atmospheric pressure if desired. Any of the conventional batch or continuous flow procedures may be used either in the liquid phase or in the vapor phase (with respect to the relatively volatile 2-methyl-3-butenenitrile reactant and linear pentenenitrile products). The reactor may be of any mechanically and chemically resistant material, and is usually of glass or an inert metal or alloy, e.g., nickel, copper, silver, gold, platinum, stainless steel, Monel®, Hastelloy®, etc.

The process is usually carried out "neat", i.e., without an added diluent or solvent. Any solvent or diluent that is nondestructive of the catalyst can be used, however. Suitable solvents include aliphatic or aromatic hydrocarbons (hexane, cyclohexane, benzene), ethers (diethyl ether, tetrahydrofuran, dioxane, glycol dimethyl ether, mole), esters (ethyl acetate, methyl benzoate), nitriles (acetonitrile, benzonitrile), etc.

A nonoxidizing environment is desirable in order to retard oxidative deactivation of the catalyst. Accordingly, an inert atmosphere, e.g., nitrogen, is normally and preferably used, although air may be used if desired at the expense of loss of a proportion of the catalyst through oxidation.

When the process is a typical batch operation in the liquid phase with or without a solvent, the catalytic nickel complex is soluble to some extent at temperatures within the operable range and is usually completely soluble at the most preferred operating temperature. However, the nickel complex is essentially nonvolatile, whereas the 2-methyl-3-butenenitrile reactant and the linear pentenenitrile products are relatively volatile. Accordingly, in a continuous flow procedure the catalyst may be a component of the flowing system in a completely liquid-phase operation, it may be in a mobile nonflowing liquid state in a semi-vapor phase operation, or it may be in a fixed-bed state (usually on a solid support) in a conventional flowing vapor-phase operation.

The time element in the process is not critical, and may generally be governed by practical considerations. The time required for a practical level of conversion of 2-methyl-3-butenenitrile to linear pentenenitriles is dependent upon the temperature of reaction, i.e., operation at lower temperature generally requires a longer time than operation at a higher temperature. A practical reaction time can be in the range of a few seconds to many hours, depending on the particular conditions and method of operation.

The molar ratio of 2-methyl-3-butenenitrile to catalyst is generally greater than 1:1, usually in the range from about 5:1 to 20,000:1, preferably 100:1 to 5,000:1, for a batch or continuous operation.

EXAMPLES

The invention will now be illustrated by the following non-limiting examples of certain preferred embodiments thereof, wherein all parts, proportions, and percentages are by weight, unless otherwise indicated. In the Examples, Ligand "A" is the ligand of Formula I, where each $R^1$ is $OCH_3$, and each $R^5$ is t-butyl.

Example 1

Butadiene Hydrocyanation

A 25 wt % solution of 1,3-butadiene was made by vacuum transfer of 11.52 g of 1,3-butadiene into 34.56 g of butyronitrile. A 25 wt % solution of HCN was made by the addition of 2.51 g of HCN to 7.50 g of propionitrile. The catalyst solution was prepared by the addition of 0.014 g of $Ni(COD)_2$, (COD)=1,5-cyclooctadiene, and 0.118 g of Ligand "A" to 9.87 g of propionitrile. With i0 these solutions, the following reaction mixtures were prepared in 2-ml GC vials equipped with micro-stirbars:

|  | Sample 1 | Sample 2 | Sample 3 |
|---|---|---|---|
| Butadiene Solution | 0.201 g | 0.201 g | 0.203 g |
| HCN Solution | 0.080 g | 0.082 g | 0.082 g |
| Catalyst Solution | 0.077 g | 0.076 g | 0.076 g |

The GC vials were crimp-sealed with caps fitted with appropriately sized l5 sheets of Nordel rubber to aid in containing the reaction mixtures. The vials were placed in a hot-block-stirrer set at 80° C. Sample 1 was removed after 1.0 hr of reaction time. Sample 2 was removed after 2.0 hrs of reaction time. Sample 3 was removed after 3.0 hrs of reaction time. The reaction was quenched in each case by diluting the reaction mixture with diglyme as a GC (gas chromatograph) solvent for product analysis. The propionitrile in the reaction mixture was used as an internal standard in the GC product analysis. The results of the analyses are shown in Table 1.

In inventive Examples 2–5, also shown in Table 1, the butadiene hydrocyanation experiments were performed essentially as described above for Example 1, except that Examples 4 and 5 were performed at 140° C. and at longer reaction times. The results are also shown in Table 1.

Comparative Example A

A 25 wt % solution of 1,3-butadiene was made by vacuum transfer of 11.52 g of 1,3-butadiene into 34.56 g of butyronitrile. A 25 wt % solution of HCN was made by the addition of 2.50 g of HCN to 7.50 g of propionitrile. The catalyst solution was prepared by the addition of 0.298 g of $Ni(pTTP)_4$, pTTP=p-tritolylphosphite, and 0.157 g of pTTP to 9.565 g of propionitrile. With these solutions, the following reaction mixtures were prepared in 2-ml GC vials equipped with micro-stirbars:

|  | Sample 1 | Sample 2 | Sample 3 |
|---|---|---|---|
| Butadiene Solution | 0.203 g | 0.215 g | 0.200 g |
| HCN Solution | 0.083 g | 0.087 g | 0.089 g |
| Catalyst Solution | 0.078 g | 0.081 g | 0.078 g |

The GC vials were crimp-sealed with caps fitted with appropriately sized sheets of Nordel rubber to aid in containing the reaction mixtures. The vials were placed in a hot-block-stirrer set at 80° C. Sample 1 was removed after 1.0 hr of reaction time. Sample 2 was removed after 2.0 hrs of reaction time. Sample 3 was removed after 3.0 hrs of reaction time. The reaction was quenched in each case by diluting the reaction mixture with diglyme as a GC solvent for product analysis. The propionitrile in the reaction mixture was used as an internal standard in the GC product analysis. The results of the analyses are shown in Table 1.

In Comparative Example B, the butadiene hydrocyanation experiment was performed essentially as described above for Comparative Example A, and the results are also shown in Table 1.

In Comparative Examples C–G, the butadiene hydrocyanation experiments were performed as described above for inventive Examples 1–5, except that the "Pringle Ligand" (compound of Formula I where $R^1$ and $R^5$=H) was used in place of Ligand "A". The results are shown in Table 1.

Example 6

2M3BN (2-methyl-3-butenenitrilie) Isomerization

The catalyst solution was prepared by the addition of 0.014 g of $Ni(COD)_2$ and 0.118 g of Ligand "A" to 9.87 g of propionitrile. A sample of 2M3BN was obtained from Fluka Chemie AG, Buchs, Switzerland and distilled under nitrogen onto 100 parts per million of 2,6-di-tert-butyl-4-methylphenol. GC analysis of this sample showed it to be 81% 2M3BN. With these mixtures, the following reaction mixtures were prepared in 2-ml GC vials equipped with micro-stirbars:

|  | Sample 1 | Sample 2 | Sample 3 |
|---|---|---|---|
| Catalyst Solution | 0.103 g | 0.100 g | 0.100 g |
| 2M3BN | 0.105 g | 0.101 g | 0.100 g |

The GC vials were crimp-sealed with caps fitted with appropriately sized sheets of Nordel rubber to aid in containing the reaction mixtures. Samples 1–3 were placed in a hot-block-stirrer set at 125° C. Sample 1 was removed after 1.0 hr of reaction time. Sample 2 was removed after 2.0 hrs of reaction time. Sample 3 was removed after 3.0 hrs of reaction time. The reaction was quenched in each case by diluting the reaction mixture with diglyme as a GC solvent for product analysis. The propionitrile in the reaction mixture was used as an internal standard in the GC product analysis. The results of the analyses are shown in Table 2.

In inventive Examples 7 and 8, the 2M3BN isomerization experiments were performed essentially as described above for Example 6, and the results are also shown in Table 2.

Comparative Example H

The catalyst solution was prepared by the addition of 0.298 g of $Ni(pTTP)_4$ and 0.157 g of pTTP to 9.565 g of propionitrile. A sample of 2M3BN was obtained from Fluka Chemie AG, Buchs, Switzerland and distilled under nitrogen onto 100 parts per million of 2,6-di-tert-butyl-4-methylphenol. GC analysis of this sample showed it to be 82% 2M3BN. With these mixtures, the following reaction mixtures were prepared in 2-ml GC vials equipped with micro-stirbars:

|  | Sample 1 | Sample 2 | Sample 3 |
| --- | --- | --- | --- |
| Catalyst Solution | 0.100 g | 0.102 g | 0.105 g |
| 2M3BN | 0.103 g | 0.106 g | 0.100 g |

The GC vials were crimp-sealed with caps fitted with appropriately sized sheets of Nordel robber to aid in containing the reaction mixtures. Samples 1–3 were placed in a hot-block-stirrer set at 125° C. Sample 1 was removed after 1.0 hr of reaction time. Sample 2 was removed after 2.0 hrs of reaction time. Sample 3 was removed after 3.0 hrs of reaction time. The reaction was quenched in each case by diluting the reaction mixture with diglyme as a GC solvent for product analysis. The propionitrile in the reaction mixture was used as an internal standard in the GC product analysis. The results of the analyses are shown in Table 2.

In Comparative Example I, the 2M3BN isomerization experiment was performed essentially as described above for Example H, and the results are also shown in Table 2.

In Comparative Examples J and K, the 2M3BN isomerization experiments were performed essentially as described above for inventive Example 6, except that the "Pringle Ligand" was used in place of Ligand "A". The results are shown in Table 2.

Stock solutions of reactants and catalyst used in inventive Examples 9–53 and 60 were made, as appropriate for the particular experiment, in the following manlier:

1,3-Butadiene Solution (BD): 25 wt % solutions of butadiene in nitrile solvent (chosen from propionitrile, butyronitrile or hexanenitrile) were made by vacuum transfer of a known quantity of butadiene into a three-fold amount of nitrile solvent. The resulting solutions were stored in a sealed vessel at –35° C. until their use in experiments.

HCN Solution: 25 wt % solutions of HCN in nitrile solvent (chosen as above) were typically made by weighing 2.50 g of liquid HCN into 7.50 g of solvent, in a glovebox. The resulting solutions were stored at –35° C. until their use in experiments.

Catalyst Solution: For a typical multidentate phosphite ligand, 1.2 mmol of P atoms and 0.055 g of Ni(COD)$_2$ (0.2 mmol) were mixed in an amount of nitrile solvent (chosen as above) such that the total solution weight would be 10.00 g. The resulting catalyst solutions were typically used immediately after mixing.

2-Methyl-3-butenenitrile Mixture (2M3BN): A sample of 2M3BN was obtained as a mixture of pentenenitrile isomers, which contains 81–82% 2M3BN.

In inventive Examples 9–31 and 53, the butadiene hydrocyanation experiments were performed as follows. The results are shown in Table 3.

To 2 mL GC vials equipped with micro-stirbars, 0.075 g of Ni catalyst solution (1.5 µmol Ni), 0.080 g of HCN stock solution (740 µmol HCN), and 0.200 g of BD stock solution (925 µmol BD) were added. The GC vial caps were fitted with appropriately sized sheets of Nordel robber to aid in containing the reaction mixtures after crimp-sealing. The vials were placed in a hot-block-stirrer set at 80° C. Samples were removed at the appropriate time points and quenched by cooling to –35° C. The reaction mixtures were then diluted in a GC solvent (chosen from glutaronitrile, diglyme or acetone) for product analysis as measured against the nitrile reaction solvent as an internal standard.

In inventive Examples 32–52 and 60, the 2M3BN isomerization experiments were performed as follows. The results are shown in Table 4.

To 2 mL GC vials equipped with micro-stirbars, 0.100 g of Ni catalyst solution (2.0 µmol Ni) and 0.100 g of the 2M3BN-containing mixture (1.0 mmol 2M3BN) were added. The GC vial caps were fitted with appropriately sized sheets of Nordel robber to aid in containing the reaction mixtures after crimp-sealing. The vials were placed in a hot-block-stirrer set at 125° C. Samples were removed at the appropriate time points and diluted in acetone for a GC solvent. The nitrile reaction solvent was used as an internal standard in the analysis and accounting of the 3PN and 2M3BN reaction product mixture.

In Tables 3 and 4, the designation "OA" represents 2-isopropylphenoxyl where the oxygen is attached to phosphorus and the designation "OC" represents 2-isopropyl-5-methylphenol where the oxygen is attached to phosphorus.

In inventive Examples 54–59, 59A, 61–66 and 66A, stock solutions of reactants and catalyst were made, as appropriate for the particular experiment, in the following manner:

1,3-Butadiene Solution (BD): 25 wt % solutions of butadiene were made by vacuum transfer of a known quantity of butadiene into a three-fold amount of toluene. The resulting solutions were stored in sealed vessels at –35° C. until their use in experiments.

HCN Solution: 25 wt % solutions of HCN were typically made by weighing 2.50 g of liquid HCN into 7.50 g of valeronitrile, in a glovebox. The resulting solutions were stored at –35° C. until their use in experiments.

Catalyst Solution: For a typical multidentate phosphite ligand, 0.84 mmol of P atoms and 0.040 g of Ni(COD)$_2$ (0.14 mmol) were mixed in an amount of either toluene or tetrahydrofuran such that the total solution weight would be 5.00 g. The resulting catalyst solutions were typically used immediately after mixing.

2-Methyl-3-butenenitrile Mixture (2M3BN): A sample of 2M3BN was obtained as a mixture of pentenenitrile isomers, which contains 81–82% 2M3BN. To 0.930 g of this mixture, 0.070 g of valeronitrile was added as an internal standard for the 2M3BN isomerization reaction.

Butadiene Hydrocyanation

In inventive Examples 54–59 and 59A, the butadiene hydrocyanation experiments were performed as follows. The results are shown in Table 5.

To 4-mL screw-capped vials equipped with micro-stirbars, 0.060 g of Ni catalyst solution (1.68 µmol Ni), 0.090 g of HCN stock solution (832 µmol HCN), and 0.200 g of BD stock solution (925 µmol BD) were added. The vials were sealed with septum caps to contain the reaction mixtures. The vials were then placed in a hot-block-stirrer set at 80° C. Samples were removed at the appropriate time points and quenched by cooling to –35° C. The reaction mixtures were then diluted in diethylether as a GC solvent for product analysis. The valeronitrile in the reaction mixtures was used as an internal standard.

Comparative Example L

A 25 wt % solution of 1,3-butadiene was made by vacuum transfer of 5.37 g of 1,3-butadiene into 16.11 g of toluene.

A 25 wt % solution of HCN was made by the addition of 1.25 g of HCN to 3.75 g of valeronitrile. The catalyst solution was prepared by the addition of 0.297 g of Ni(pTTP)$_4$ and 0.155 g of pTTP to 6.71 g of toluene. With these solutions, the following reaction mixtures were prepared in 4-ml screw-capped vials equipped with microstirbars:

|  | Sample 1 | Sample 2 |
|---|---|---|
| Butadiene Solution | 0.207 g | 0.208 g |
| HCN Solution | 0.091 g | 0.089 g |
| Catalyst Solution | 0.059 g | 0.077 g |

The vials were sealed with septum caps to contain the reaction mixtures. The vials were placed in a hot-block-stirrer set at 80° C. Sample 1 was removed after 1.5 h of reaction time. Sample 2 was removed after 2.5 h of reaction time. The reaction was quenched in each case by cooling the reaction mixture to −35° C. The reaction mixtures were then diluted in diethylether as a GC solvent for product analysis. The valeronitrile in the reaction mixture was used as an internal standard. The results of the analyses are shown in Table 5.

In Comparative Example M, the butadiene hydrocyanation experiment was I 0 performed essentially as described above for Example L, and the results are also shown in Table 5.

2M3BN Isomerization

In inventive Examples 61–66 and 66A, the 2M3BN isomerization experiments were performed as follows. The results are shown in Table 6.

To 4-mL screw-capped vials equipped with microstirbars, 0.070 g of Ni catalyst solution (2.0 μmol Ni) and 0.107 g of the 2M3BN-containing mixture (1.0 mmol 2M3BN) were added. The vials were sealed with septum caps to contain the reaction mixtures. The vials were then placed in a hot-block-stirrer set at 125° C. Samples were removed at the appropriate time points and quenched by cooling to −35° C. The reaction mixtures were then diluted in diethylether as a GC solvent for product analysis. The valeronitrile in the reaction mixtures was used as an internal standard in the analysis and accounting of the 3PN and 2M3BN reaction product mixture.

Comparative Example N

A 25 wt % solution of 1,3-butadiene was made by vacuum transfer of 5.37 g of 1,3-butadiene into 16.11 g of toluene. A 25 wt % solution of HCN was made by the addition of 1.25 g of HCN to 3.75 g of valeronitrile. The catalyst solution was prepared by the addition of 0.297 g of Ni(pTTP)$_4$ and 0.155 g of pTTP to 6.71 g of toluene. With these solutions, the following reaction mixtures were prepared in 4-ml screw-capped vials equipped with microstirbars:

|  | Sample 1 | Sample 2 |
|---|---|---|
| Catalyst Solution | 0.074 g | 0.073 g |
| 2M3BN | 0.106 g | 0.106 g |

The vials were sealed with septum caps to contain the reaction mixtures. The vials were placed in a hot-block-stirrer set at 125° C. Sample 1 was removed after 1.5 h of reaction time. Sample 2 was removed after 2.5 h of reaction time. The reaction was quenched in each case by cooling the reaction mixture to −35° C. The reaction mixtures were then diluted in diethylether as a GC solvent for product analysis. The valeronitrile in the reaction mixture was used as an internal standard in the analysis and accounting of the 3PN and 2M3BN reaction product mixture. The results of the analyses are shown in Table 6.

In Comparative Example 0, the 2M3BN isomerization experiment was performed essentially as described above for Example N, and the results are also shown in Table 6.

TABLE 1

Step 1 - Hydrocyanation Reaction

| Example | Catalyst | Molar Ratio P/Ni | Molar Ratio HCN/Ni | Reaction Time | Temperature | % Yield 3PN | % Yield 2M3BN | % Yield Total PN |
|---|---|---|---|---|---|---|---|---|
| 1 | Ligand A Ni(COD)2 | 6 | 2000 | 1 hr 3 hr | 80° C. | 19.1 21.5 | 75.5 76.3 | 94.7 97.8 |
| 2 | Ligand A Ni(COD)2 | 6 | 2000 | 1 hr 3 hr | 80° C. | 17.3 18.3 | 71.2 73.3 | 88.5 91.6 |
| 3 | Ligand A Ni(COD)2 | 6 | 2000 | 1 hr | 80° C. | 18.8 | 76.9 | 95.6 |
| A | Ni(pTTP)4 pTTP | 6 | 500 | 1 hr 2 hr 3 hr | 80° C. | 2.1 3.5 4.7 | 1.6 2.4 3.0 | 3.7 6.0 7.7 |
| B | Ni(pTTP)4 pTTP | 6 | 500 | 1 hr 2 hr 3 hr | 80° C. | 2.8 4.7 6.3 | 1.7 2.8 3.7 | 4.5 7.5 10.1 |
| C | Pringle Ligand Ni(COD)2 | 6 | 2000 | 1 hr 2 hr 3 hr | 80° C. | 0.0 0.0 0.0 | 0.0 0.0 0.0 | 0.0 0.0 0.0 |
| D | Pringle Ligand Ni(COD)2 | 6 | 2000 | 1 hr 2 hr 3 hr | 80° C. | 0.0 0.0 0.0 | 0.0 0.0 0.0 | 0.0 0.0 0.0 |
| 4 | Ligand A Ni(COD)2 | 6 | 2000 | 1 hr 5 hr | 140° C. | 26.2 26.8 | 63.4 64.1 | 89.6 90.9 |
| 5 | Ligand A Ni(COD)2 | 6 | 2000 | 5 hr | 140° C. | 31.7 | 59.6 | 91.3 |
| E | Pringle Ligand | 6 | 2000 | 1 hr | 140° C. | 2.1 | 2.0 | 4.1 |

TABLE 1-continued

Step 1 - Hydrocyanation Reaction

| Example | Catalyst | Molar Ratio P/Ni | Molar Ratio HCN/Ni | Reaction Time | Temperature | % Yield 3PN | % Yield 2M3BN | % Yield Total PN |
|---|---|---|---|---|---|---|---|---|
|  | Ni(COD)2 |  |  | 5 hr |  | 5.3 | 4.8 | 10.1 |
| F | Pringle Ligand | 6 | 2000 | 1 hr | 140° C. | 2.1 | 2.0 | 4.1 |
|  | Ni(COD)2 |  |  | 5 hr |  | 5.1 | 4.6 | 9.7 |
| G | Pringle Ligand | 6 | 2000 | 1 hr | 140° C. | 1.0 | 1.0 | 2.0 |
|  | Ni(COD)2 |  |  | 5 hr |  | 6.8 | 6.0 | 12.8 |

Ligand A = Compound of Formula I where $R^1$ = $OCH_3$ and $R^5$ = t-butyl

Pringle Ligand = Compound of Formula I where $R^1$ and $R^5$ = H made according to the teachings of Baker et al., J. Chem. Soc., Chem. Commun., 1991, pp. 803-804 pTTP = tri-para tolyl phosphite the catalysts of which are mentioned in U.S. Pat. No. 3,536,748

TABLE 2

Step 2 - Isomerization Reaction

| Example | Catalyst | Molar Ratio P/Ni | Initial Ratio 2M3BN/Ni | Reaction Time | Temperature | Ratio 3PN/2M3BN | 3PN / 3PN + 2M3BN | 3PN + 2M3BN Accounting |
|---|---|---|---|---|---|---|---|---|
| 6 | Ligand A | 6 | 2000 | 1 hr | 125° C. | 0.6 | 39.0% | 98.9% |
|  | Ni(COD)2 |  |  | 2 hr |  | 2.9 | 74.4% | 100.0% |
|  |  |  |  | 3 hr |  | 12.9 | 92.8% | 100.0% |
| 7 | Ligand A | 6 | 2000 | 2 hr | 125° C. | 12.0 | 92.3% | 96.3% |
|  | Ni(COD)2 |  |  | 3 hr |  | 13.8 | 93.2% | 100.0% |
| 8 | Ligand A | 6 | 2000 | 1 hr | 125° C. | 3.7 | 78.6% | 100.0% |
|  | Ni(COD)2 |  |  | 2 hr |  | 10.1 | 91.0% | 100.0% |
| H | Ni(pTTP)4 | 6 | 500 | 1 hr | 125° C. | 0.1 | 10.7% | 100.0% |
|  | pTTP |  |  | 2 hr |  | 0.2 | 17.5% | 100.0% |
|  |  |  |  | 3 hr |  | 0.3 | 24.6% | 99.8% |
| I | Ni(pTTP)4 | 6 | 500 | 1 hr | 125° C. | 0.2 | 14.3% | 92.6% |
|  | pTTP |  |  | 2 hr |  | 0.4 | 30.3% | 86.5% |
| J | Pringle Ligand | 6 | 2000 | 1 hr | 125° C. | 0.0 | 0.5% | 100.0% |
|  | Ni(COD)2 |  |  | 2 hr |  | 0.0 | 0.5% | 94.2% |
|  |  |  |  | 4 hr |  | 0.0 | 0.5% | 82.3% |
| K | Pringle Ligand | 6 | 2000 | 1 hr | 125° C. | 0.0 | 0.5% | 98.1% |
|  | Ni(COD)2 |  |  | 2 hr |  | 0.0 | 0.5% | 100.0% |

Ligand A = Compound of Formula I where $R^1$ = $OCH_3$ and $R^5$ = t-butyl

Pringle Ligand = Compound of Formula I where $R^1$ and $R^5$ = H made according to the teachings of Baker et al., J. Chem. Soc., Chem. Commun., 1991, pp. 803-804 pTTP = tri-para tolyl phosphite the catalysts of which are mentioned in U.S. Pat. No. 3,536,748

TABLE 3

Step 1 - Hydrocyanation Reaction

| Example | Ligand | Reaction Time | % Yield 3PN | % Yield 2M3BN | % Yield Total PN |
|---|---|---|---|---|---|
| 9 | 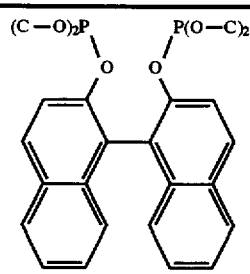 Formula XI | 1 hr | 25.8 | 53.9 | 79.8 |
|  |  | 2 hr | 33.3 | 62.4 | 95.7 |
|  |  | 3 hr | 36.0 | 60.9 | 96.9 |

TABLE 3-continued

Step 1 - Hydrocyanation Reaction

| Example | Ligand | Reaction Time | % Yield 3PN | % Yield 2M3BN | % Yield Total PN |
|---|---|---|---|---|---|
| 10 | Formula VII | 1 hr | 46.0 | 39.0 | 85.0 |
|  |  | 2 hr | 42.7 | 34.7 | 77.4 |
|  |  | 3 hr | 49.8 | 40.2 | 90.0 |
| 11 | Formula I | 1 hr | 20.6 | 33.7 | 54.3 |
|  |  | 2 hr | 30.9 | 50.7 | 81.6 |
|  |  | 3 hr | 33.9 | 55.3 | 89.2 |
| 12 | Formula I | 1 hr | 27.9 | 49.1 | 77.0 |
|  |  | 2 hr | 31.5 | 53.6 | 85.1 |
|  |  | 3 hr | 34.2 | 55.0 | 89.1 |
| 13 | Formula XI | 1 hr | 29.6 | 61.3 | 90.9 |
|  |  | 2 hr | 29.5 | 60.9 | 90.3 |
|  |  | 3 hr | 29.1 | 59.9 | 88.9 |
| 14 | Formula VII | 1 hr | 21.0 | 52.7 | 73.7 |
|  |  | 2 hr | 26.3 | 58.7 | 85.0 |
|  |  | 3 hr | 25.9 | 62.6 | 88.5 |
| 15 | Formula XIII | 1 hr | 40.1 | 24.7 | 64.8 |
|  |  | 2 hr | 55.8 | 33.9 | 89.7 |
|  |  | 3 hr | 54.5 | 32.9 | 87.4 |

TABLE 3-continued

Step 1 - Hydrocyanation Reaction

| Example | Ligand | Reaction Time | % Yield 3PN | % Yield 2M3BN | % Yield Total PN |
|---|---|---|---|---|---|
| 16 | 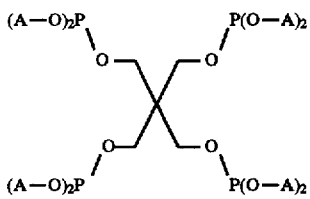<br>Formula XIV | 1 hr<br>2 hr<br>3 hr | 52.9<br>51.8<br>52.5 | 34.6<br>33.7<br>33.9 | 87.5<br>85.4<br>86.4 |
| 17 | 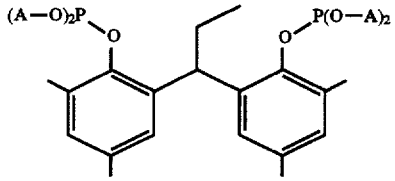<br>Formula VII | 1 hr<br>2 hr<br>3 hr | 21.6<br>24.9<br>30.1 | 39.7<br>45.9<br>54.5 | 61.3<br>70.8<br>84.6 |
| 18 | 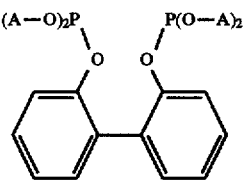<br>Formula I | 1 hr<br>2 hr<br>3 hr | 29.0<br>30.3<br>30.2 | 53.5<br>55.5<br>53.2 | 82.4<br>85.8<br>83.3 |
| 19 | 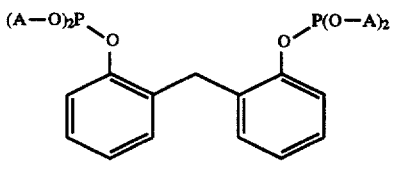<br>Formula VII | 1 hr<br>2 hr<br>3 hr | 24.7<br>26.0<br>41.8 | 23.6<br>25.2<br>40.3 | 48.3<br>51.2<br>82.1 |
| 20 | 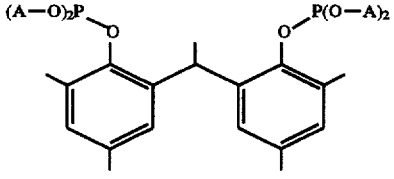<br>Formula VII | 1 hr<br>2 hr<br>3 hr | 27.0<br>28.3<br>28.9 | 49.0<br>51.2<br>52.2 | 76.0<br>79.4<br>81.1 |
| 21 | 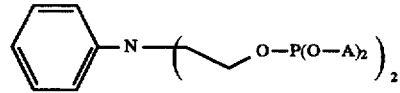<br>Formula XV | 1 hr<br>2 hr<br>3 hr | 8.3<br>22.2<br>20.2 | 5.9<br>15.6<br>14.3 | 14.2<br>37.9<br>34.5 |

TABLE 3-continued

Step 1 - Hydrocyanation Reaction

| Example | Ligand | Reaction Time | % Yield 3PN | % Yield 2M3BN | % Yield Total PN |
|---|---|---|---|---|---|
| 22 | Formula III | 1.5 hr | 7.2 | 33.6 | 40.7 |
|  |  | 2 hr | 7.5 | 34.8 | 42.3 |
|  |  | 3 hr | 8.0 | 37.7 | 45.8 |
| 23 | Formula III | 1 hr | 13.8 | 26.5 | 40.3 |
|  |  | 2 hr | 16.4 | 31.7 | 48.1 |
|  |  | 3 hr | 14.4 | 27.8 | 42.2 |
| 24 | Formula III | 1 hr | 6.5 | 26.1 | 32.6 |
|  |  | 2 hr | 7.7 | 27.1 | 34.8 |
|  |  | 3 hr | 8.9 | 32.6 | 41.5 |
| 25 | Formula XII | 1 hr | 33.2 | 25.8 | 59.0 |
|  |  | 2 hr | 36.9 | 28.6 | 65.6 |
|  |  | 3 hr | 44.2 | 34.1 | 78.4 |

TABLE 3-continued

Step 1 - Hydrocyanation Reaction

| Example | Ligand | Reaction Time | % Yield 3PN | % Yield 2M3BN | % Yield Total PN |
|---|---|---|---|---|---|
| 26 | (C—O)₂P—O—[phenyl]—O—[phenyl]—O—P(O—C)₂<br>Formula VII | 1 hr<br>2 hr<br>3 hr | 44.8<br>44.5<br>49.5 | 23.7<br>23.5<br>24.7 | 68.5<br>68.0<br>74.2 |
| 27 | (C—O)₂P—O—[dimethylphenyl]—CH(Et)—[dimethylphenyl]—O—P(O—C)₂<br>Formula VII | 1 hr<br>2 hr<br>3 hr | 16.9<br>18.9<br>18.8 | 46.2<br>51.5<br>52.0 | 63.1<br>70.3<br>70.9 |
| 28 | (A—O)₂P—O—[4-Cl-phenyl]—CH₂—[4-Cl-phenyl]—O—P(O—A)₂<br>Formula VII | 1 hr<br>2 hr<br>3 hr | 28.1<br>32.7<br>33.2 | 29.3<br>33.5<br>34.4 | 57.3<br>66.2<br>67.6 |
| 29 | (C—O)₂P—O—[4-OMe-phenyl]—CH₂—[4-OMe-phenyl]—O—P(O—C)₂<br>Formula VII | 1 hr<br>2 hr<br>3 hr | 27.4<br>34.7<br>35.8 | 22.3<br>26.8<br>28.2 | 49.7<br>61.6<br>64.0 |
| 30 | (C—O)₂P—O—[4-Cl-phenyl]—CH₂—[4-Cl-phenyl]—O—P(O—C)₂<br>Formula VII | 1 hr<br>2 hr<br>3 hr | 18.9<br>21.6<br>27.1 | 17.7<br>20.8<br>25.1 | 36.7<br>42.5<br>52.1 |
| 31 | C—(O—P(O—C)₂)₄<br>Formula XIV | 1 hr<br>2 hr<br>3 hr | 26.8<br>12.9<br>28.6 | 20.6<br>9.5<br>22.2 | 47.4<br>22.4<br>50.8 |

TABLE 3-continued

Step 1 - Hydrocyanation Reaction

| Example | Ligand | Reaction Time | % Yield 3PN | % Yield 2M3BN | % Yield Total PN |
|---|---|---|---|---|---|
| 53 | Formula IV | 1 hr | 21.9 | 44.1 | 66.0 |
|  |  | 2 hr | 26.9 | 53.3 | 80.2 |
|  |  | 3 hr | 31.6 | 62.2 | 93.9 |

TABLE 4

Step 2 - Isomerization Reaction

| Example | Ligand | Reaction Time | % Yield 2M3BN | % Yield 3PN | Ratio 3PN/2M3BN | 2PN + 2M3BN Accounting |
|---|---|---|---|---|---|---|
| 32 | Formula XI | 0 hr | 100.4% | 1.2% | 0.01 | 101.6% |
|  |  | 1 hr | 8.7% | 91.4% | 10.51 | 100.1% |
|  |  | 2 hr | 6.0% | 96.5% | 16.11 | 102.5% |
|  |  | 3 hr | 6.2% | 93.4% | 15.12 | 99.6% |
| 33 | Formula VII | 0 hr | 96.6% | 1.3% | 0.01 | 97.9% |
|  |  | 1 hr | 19.4% | 75.7% | 3.90 | 95.1% |
|  |  | 2 hr | 12.3% | 86.3% | 7.02 | 98.6% |
|  |  | 3 hr | 7.8% | 89.3% | 11.51 | 97.0% |
| 34 | Formula I | 0 hr | 100.0% | 1.3% | 0.01 | 101.3% |
|  |  | 1 hr | 44.0% | 57.1% | 1.30 | 101.1% |
|  |  | 2 hr | 19.6% | 80.4% | 4.10 | 100.0% |
|  |  | 3 hr | 16.2% | 85.8% | 5.30 | 101.9% |

TABLE 4-continued

Step 2 - Isomerization Reaction

| Example | Ligand | Reaction Time | % Yield 2M3BN | % Yield 3PN | Ratio 3PN/2M3BN | 2PN + 2M3BN Accounting |
|---|---|---|---|---|---|---|
| 35 | (A—O)₂P-O-[phenyl]-O-[phenyl]-O-P(O—A)₂ Formula VII | 0 hr<br>1 hr<br>2 hr<br>3 hr | 104.7%<br>51.1%<br>32.3%<br>24.0% | 1.2%<br>49.3%<br>73.5%<br>80.6% | 0.01<br>0.96<br>2.27<br>3.35 | 105.9%<br>100.4%<br>105.9%<br>104.6% |
| 36 | (C—O)₂P-O-[phenyl]-O-[phenyl]-O-P(O—C)₂ Formula VII | 0 hr<br>1 hr<br>2 hr<br>3 hr | 94.3%<br>5.4%<br>5.8%<br>5.2% | 1.1%<br>82.6%<br>89.6%<br>79.6% | 0.01<br>15.39<br>15.36<br>15.19 | 95.4%<br>87.9%<br>95.4%<br>84.9% |
| 37 | (C—O)₂P-O-[substituted diphenyl propane]-O-P(O—C)₂ Formula VII | 0 hr<br>1 hr<br>2 hr<br>3 hr | 99.0%<br><br>23.8%<br>19.5% | 1.2%<br><br>74.8%<br>79.2% | 0.01<br><br>3.15<br>4.07 | 100.2%<br><br>98.5%<br>98.7% |
| 38 | (A—O)₂P—O-[substituted diphenyl methane]-O—P(O—A)₂ Formula VII | 0 hr<br>1 hr<br>2 hr<br>3 hr | 100.6%<br>47.8%<br>31.6%<br>20.8% | 1.1%<br>51.1%<br>67.8%<br>77.9% | 0.01<br>1.07<br>2.14<br>3.75 | 101.7%<br>98.9%<br>99.4%<br>98.7% |
| 39 | PhN(CH₂CH₂O—P(O—C)₂)₂ Formula XV | 0 hr<br>1 hr<br>2 hr<br>3 hr | 107.6%<br><br>10.1%<br>6.1% | 1.4%<br><br>97.5%<br>103.2% | 0.01<br><br>9.62<br>17.05 | 108.9%<br>107.6%<br>109.3% |
| 40 | O—P(O—C)₂ O—P(O—C)₂ [biphenyl with OMe groups] Formula I | 0 hr<br>1 hr<br>2 hr<br>3 hr | 103.5%<br>46.0%<br>10.4%<br>6.3% | 1.2%<br>54.9%<br>90.2%<br>101.8% | 0.01<br>1.19<br>8.68<br>16.27 | 104.7%<br>101.0%<br>100.6%<br>108.1% |
| 41 | (C—O)₂P—O-[diphenylmethane with OMe]-O—P(O—C)₂ Formula VII | 0 hr<br>1 hr<br>2 hr<br>3 hr | 100.6%<br>11.0%<br>6.5%<br>6.4% | 1.4%<br>91.8%<br>102.9%<br>100.9% | 0.01<br>8.33<br>15.94<br>15.69 | 101.9%<br>102.8%<br>109.4%<br>107.3% |

TABLE 4-continued

Step 2 - Isomerization Reaction

| Example | Ligand | Reaction Time | % Yield 2M3BN | % Yield 3PN | Ratio 3PN/2M3BN | 2PN + 2M3BN Accounting |
|---|---|---|---|---|---|---|
| 42 | 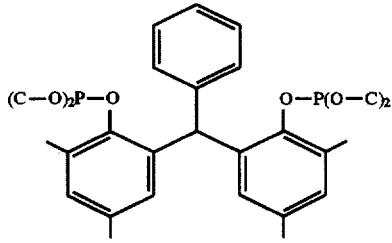<br>Formula VII | 0 hr<br>1 hr<br>2 hr<br>3 hr | 99.7%<br><br>5.7%<br>5.7% | 1.2%<br><br>99.6%<br>100.5% | 0.01<br><br>17.47<br>17.61 | 100.9%<br><br>105.2%<br>106.2% |
| 43 | 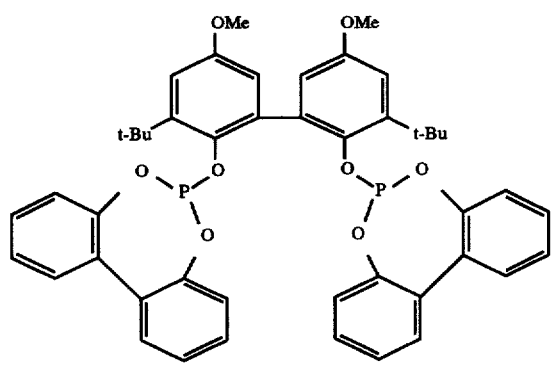<br>Formula I | 0 hr<br>1 hr<br>2 hr<br>3 hr | 103.3%<br>63.0%<br>27.1%<br>7.7% | 1.2%<br>40.3%<br>78.9%<br>99.2% | 0.01<br>0.64<br>2.91<br>12.89 | 104.5%<br>103.3%<br>106.0%<br>106.9% |
| 44 | 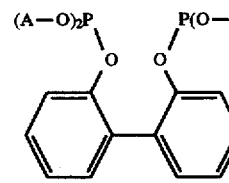<br>Formula I | 0 hr<br>1 hr<br>2 hr<br>3 hr | 101.3%<br>42.9%<br>27.0%<br>22.5% | 1.3%<br>58.4%<br>73.6%<br>77.7% | 0.01<br>1.36<br>2.73<br>3.46 | 102.6%<br>101.3%<br>100.6%<br>100.2% |
| 45 | 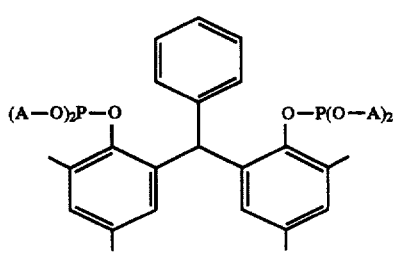<br>Formula VII | 0 hr<br>1 hr<br>2 hr<br>3 hr | 101.3%<br>59.6%<br>39.6%<br>28.3% | 1.2%<br>45.5%<br>60.0%<br>73.0% | 0.01<br>0.76<br>1.51<br>2.58 | 102.5%<br>105.1%<br>99.6%<br>101.4% |
| 46 | 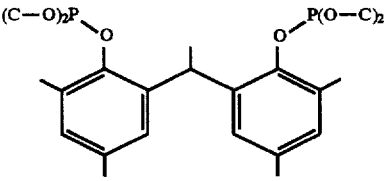<br>Formula VII | 0 hr<br>1 hr<br>2 hr<br>3 hr | 98.9%<br>22.7%<br>22.0%<br>25.2% | 1.8%<br>76.2%<br>75.8%<br>72.4% | 0.02<br>3.37<br>3.44<br>2.88 | 100.7%<br>98.9%<br>97.8%<br>97.6% |

TABLE 4-continued

Step 2 - Isomerization Reaction

| Example | Ligand | Reaction Time | % Yield 2M3BN | % Yield 3PN | Ratio 3PN/2M3BN | 2PN + 2M3BN Accounting |
|---|---|---|---|---|---|---|
| 47 | Formula XII | 0 hr | 82.2% | 0.9% | 0.01 | 83.2% |
|  |  | 1 hr | 37.2% | 52.3% | 1.40 | 89.5% |
|  |  | 2 hr | 20.2% | 63.4% | 3.13 | 83.6% |
|  |  | 3 hr | 23.2% | 67.0% | 2.89 | 90.2% |
| 48 | Formula XV | 0 hr | 89.3% | 1.0% | 0.01 | 90.3% |
|  |  | 1 hr | 56.9% | 36.3% | 0.64 | 93.3% |
|  |  | 2 hr | 47.3% | 55.0% | 1.16 | 102.3% |
|  |  | 3 hr | 44.0% | 53.2% | 1.21 | 97.2% |
| 49 | Formula VII | 0 hr | 70.1% | 0.9% | 0.01 | 71.0% |
|  |  | 1 hr | 23.5% | 54.9% | 2.34 | 78.4% |
|  |  | 2 hr | 20.1% | 51.9% | 2.59 | 72.0% |
|  |  | 3 hr | 23.0% | 52.7% | 2.29 | 75.7% |
| 50 | Formula VIII | 0 hr | 100.1% | 1.3% | 0.01 | 101.4% |
|  |  | 1 hr | 76.9% | 24.2% | 0.31 | 101.1% |
|  |  | 2 hr | 56.7% | 44.8% | 0.79 | 101.5% |
|  |  | 3 hr | 52.1% | 50.4% | 0.97 | 102.5% |
| 51 | Formula I | 0 hr | 97.1% | 1.1% | 0.01 | 98.2% |
|  |  | 1 hr | 67.2% | 30.2% | 0.45 | 97.4% |
|  |  | 2 hr | 57.0% | 41.6% | 0.73 | 98.7% |
|  |  | 3 hr | 45.6% | 48.6% | 1.07 | 94.2% |
| 52 | Formula XIV | 0 hr | 94.4% | 1.1% | 0.01 | 95.5% |
|  |  | 1 hr | 46.1% | 52.3% | 1.13 | 98.5% |
|  |  | 2 hr | 41.1% | 51.6% | 1.25 | 92.8% |
|  |  | 3 hr | 27.5% | 44.4% | 1.61 | 71.9% |

TABLE 4-continued

Step 2 - Isomerization Reaction

| Example | Ligand | Reaction Time | % Yield 2M3BN | % Yield 3PN | Ratio 3PN/2M3BN | 2PN + 2M3BN Accounting |
|---|---|---|---|---|---|---|
| 60 | Formula IV | 2 hr | 10.5 | 86.7 | 8.28 | 97.1 |

TABLE 5

BD Hydrocyanation

| Example | Ligand | Reaction Time | % Yield 3PN | % Yield 2M3 | Total |
|---|---|---|---|---|---|
| 54 | Formula VII | 2 hr<br>3 hr | 40.8<br>42.2 | 31.8<br>33.7 | 72.6<br>75.9 |
| 55 | Formula VII | 2 hr<br>3 hr | 47.8<br>47.5 | 34.8<br>34.4 | 82.7<br>81.9 |

TABLE 5-continued

BD Hydrocyanation

| | | | | | |
|---|---|---|---|---|---|
| 56 | *(structure, Formula XI, with OEt substituents)* | 2 hr | 47.4 | 38.8 | 86.2 |
| | | 3 hr | 47.0 | 38.0 | 85.0 |
| 57 | *(structure, Formula XI, with OMe substituents)* | 2 hr | 42.6 | 34.0 | 76.6 |
| | | 3 hr | 46.7 | 35.5 | 82.2 |
| 58 | *(structure, Formula XI, with OCH$_2$Ph substituents)* | 2 hr | 48.0 | 38.1 | 86.0 |
| | | 3 hr | 46.9 | 38.1 | 85.0 |
| 59 | *(structure, Formula XI)* | 2 hr | 34.9 | 18.9 | 53.9 |
| | | 3 hr | 51.0 | 30.3 | 81.3 |

TABLE 5-continued

BD Hydrocyanation

| 59A | [structure: Formula XI — biphenyl/binaphthyl bisphosphite with MeO and OMe substituents] | 2 hr | 35.0 | 38.8 | 73.3 |
| --- | --- | --- | --- | --- | --- |
|  |  | 3 hr | 34.9 | 38.5 | 73.4 |

Formula XI

| Comparative Example | Catalyst | Reaction Time | % Yield 3PN | % Yield 2M3 | Total |
| --- | --- | --- | --- | --- | --- |
| L | Ni(pTTP)₄/pTTP | 1.5 hr | 7.4 | 4.1 | 11.5 |
|  |  | 2.5 hr | 12.3 | 6.6 | 18.9 |
| M | Ni(pTTP)₄/pTTP | 2 hr | 3.8 | 1.7 | 5.5 |
|  |  | 3 hr | 8.2 | 4.5 | 12.7 |

TABLE 6

2M3 Isomerization

| Example | Ligand | Reaction Time | % Yield 2M3 | % Yield 3PN | % 3PN/2M3 Ratio | Accounting |
| --- | --- | --- | --- | --- | --- | --- |
| 61 | [structure — Formula VII with OMe substituents] | 2 hr | 14.7 | 113.4 | 7.72 | 128.1 |
| 62 | [structure — Formula VII] | 2 hr | 49.0 | 63.4 | 1.30 | 112.4 |

Formula VII

Formula VII

TABLE 6-continued

| | 2M3 Isomerization | | | | | |
|---|---|---|---|---|---|---|
| 63 | Formula XI | 2 hr | 45.2 | 54.3 | 1.20 | 99.5 |
| | | 3 hr | 35.6 | 66.3 | 1.86 | 101.9 |
| 64 | Formula XI | 2 hr | 14.3 | 81.7 | 5.70 | 96.0 |
| | | 3 hr | 11.9 | 83.0 | 6.95 | 94.9 |
| 65 | Formula XI | 2 hr | 8.5 | 86.8 | 10.3 | 95.2 |
| | | 3 hr | 8.1 | 86.2 | 10.6 | 94.3 |
| 66 | Formula XI | 2 hr | 28.4 | 65.4 | 2.30 | 93.8 |
| | | 3 hr | 14.9 | 77.8 | 5.23 | 92.7 |

TABLE 6-continued

2M3 Isomerization

| Catalyst | Comparative Example | Reaction Time | % Yield 2M3 | % Yield 3PN | 3PN/2M3 Ratio | Accounting |
|---|---|---|---|---|---|---|
| 66A | 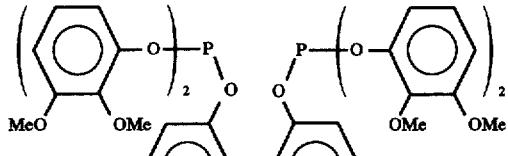 Formula XI (MeO, OMe, OMe, OMe) | 2 hr | 26.3 | 72.6 | 2.80 | 98.9 |
| N | Ni(pTTP)$_4$/pTTP | 1.5 hr | 58.5 | 32.1 | 0.55 | 90.6 |
|  |  | 2.5 hr | 61.7 | 33.4 | 0.54 | 95.1 |
| O | Ni(pTTO)$_4$/pTTP | 2 hr | 64.8 | 31.5 | 0.49 | 96.3 |
|  |  | 3 hr | 49.5 | 44.0 | 0.89 | 93.4 |

Preparation of ligands containing ortho substituted oxygen containing groups are shown below.

Example 67

Ligand B; Formula VI where R$^2$ is the cyclic group, —O—C(CH$_3$)$_2$—CH$_2$—

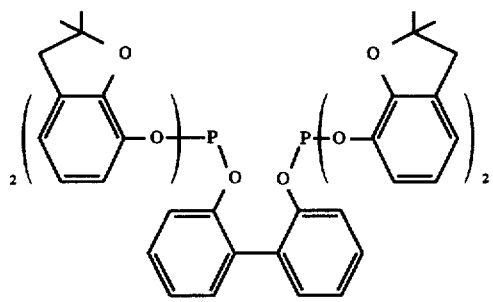

The chlorodite derived from 2,3-dihydro-2,2-dimethyl-7-benzofuranol was prepared in situ from PCl$_3$ and 2,3-dihydro-2,2-dimethyl-7-benzofuranol. A toluene solution containing 0.55 g (4 mmoles) of PCl$_3$ and 1.314 g (8 mmoles) of 2,3-dihydro-2,2-dimethyl-7-benzofuranol was cooled to −30° C. A chilled toluene solution (−30° C.) containing 1.0 g (10 mmoles) of NEt$_3$ was slowly added dropwise to the above solution. The mixture was stirred overnight to give a solution of the chlorodite ($^{31}$P nmr in toluene/CDCl$_3$: 165 ppm). A toluene solution containing 0.372 g (2 mmoles) of 2,2'-biphenol and 0.6 g (6 mmoles) of NEt$_3$ was added and the mixture was allowed to stiirred overnight. The mixture was filtered through celite, washed with toluene and solvent removed to give 1.84 g of the desired product. $^{31}$P nmr in C$_6$D$_6$: 131.9 ppm along with small peaks due to impurities at 146,133,132 ppm. FABMS (fast atom bombardment mass spectroscopy): Found: 899.23; calculated M+H with M=C$_{52}$H$_{52}$O$_{10}$P$_2$: 899.31.

Example 68

Ligand C; Formula XI where R$^2$ is the cyclic group, —O—C(CH$_3$)$_2$—CH$_2$—

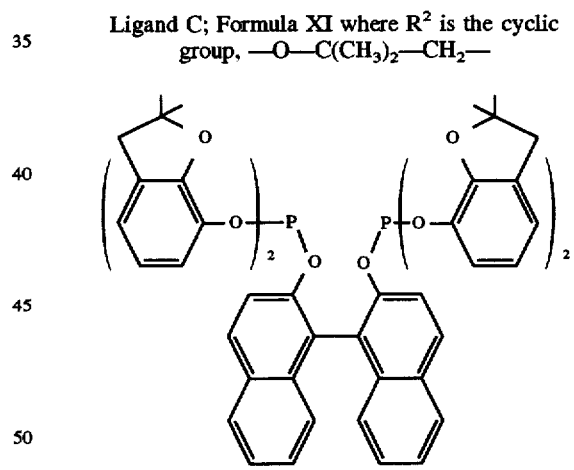

Ligand C was prepared similarly to Ligand B. 0.57 g (2 mmoles) of 1,1'-bi-2-naphthol was used instead of biphenol. After the usual workup, 1.97 g of product was obtained as a white solid. $^{31}$P (ppm, C$_6$D$_6$): 131.26 with minor peaks at 147.3,133.1,131.5, and 131.0. FABMS (fast atom bombardment mass spectroscopy): Found: 999.24; calculated M+H with M=C$_{60}$H$_{56}$O$_{10}$P$_2$: 999.33.

Example 69

Ligand D; Formula XX where R² is OMe

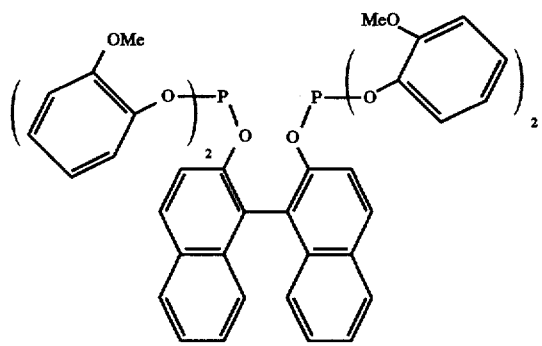

The chlorodite derived from guaiacol was prepared in situ from PCl₃ and guaiacol. A toluene solution containing 0.55 g (4 moles) of PCl₃ and 0.993 g (8 mmoles) of guaiacol was cooled to −30° C. A chilled toluene solution (−30° C.) containing 1.0 g (10 mmoles) of NEt₃ was slowly added dropwise to the above solution. The mixture was stirred for 45 minutes at room temperature to give a solution of the chlorodite (31p (ppm, C₆D₆/toluene): 166.17). A toluene solution containing 0.573 g (2 mmoles) of 1,1'-bi-2-naphthol and 0.6 g (6 mmoles) of NEt₃ was added and the mixture was allowed to stirred overnight. The mixture was filtered through celite, washed with toluene and solvent removed to give 1.67 g of the desired product. ³¹P nmr in C₆D₆: 131.7 ppm along with small peaks due to impurities at 147, 133, 128 ppm. This material was purified by flash column chromatography on silica gel eluted with 10–20% EtOAc/hexane to give the product as a white paste. ¹H nmr (δ, CDCl₃): 3.61 (s, 6H), 3.62 (s, 6H), 6.62–7.92 (m, 28H). ³P nmr (ppm, CDCl₃): 132.04. FABMS (fast atom bombardment mass spectroscopy): Found: 837.03; calculated M−H with M=C₄₈H₄₀O₁₀P₂: 837.21.

Example 70

Ligand E; Formula VIII with X is CH(Et) and R² is —OCH₂—Ph

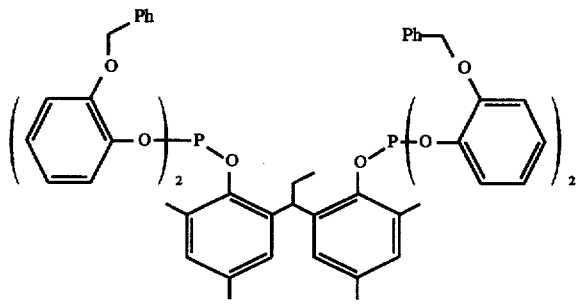

Prepared similarly to Ligand B but used 1.602 g of 2-(benzyloxy)phenol instead of 2,3-dihydro-2,2-dimethyl-7-benzofuranol and 541 mg (1.9 mmoles) of 2,2'-propylidenebis(4,6-dimethylphenol) (prepared according to Yamada et at., Bull. Chem. Soc. Jpn., 62, 3603 (1989)) instead of 2,2'-biphenol. After the usual workup, 2.167 g of a light tan paste was obtained. ³¹P (ppm, C₆D₆): 135.73 with minor peak at 132.8. FABMS (fast atom bombardment mass spectroscopy): Found: 1139.27; calculated M−H with M=C₇₁H₆₆O₁₀P₂: 1139.40.

Example 71

Ligand F; Formula VI with R⁵' is H and R² is —OCH₂Ph

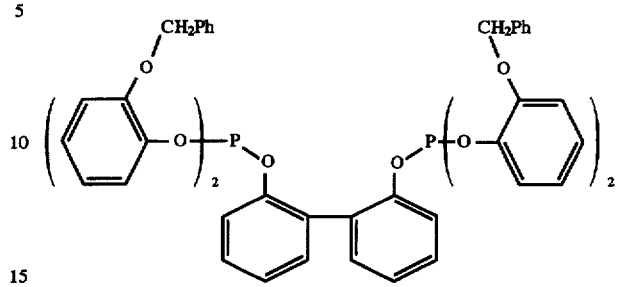

Prepared similarly to Ligand B but used 1.602 g of 2-(benzyloxy)phenol instead of 2,3-dihydro-2,2-dimethyl-7-benzofuranol. After the usual workup, 2.099 g of a light tan paste was obtained. ³¹P (ppm, C₆D₆): 131.95 with minor peaks at 146.6, 132.9. FABMS (fast atom bombardment mass spectroscopy): Found: 1043.24; calculated M+H with M=C₆₄H₅₂O₁₀P₂: 1043.31.

Examples 72 and 73 describe preparation of phosphorochloridite using N,N-dialkyl diarylphosphoramidite.

Example 72

A. Bis[(2-isopropyl-5-methyl)phenyl]N,N-diisopropylphosphoramidite:

To solution of 25.0 g of PCl₃ in 350 mL of dry toluene was added 19.1 g of dry diisopropylamine, maintaining the temperature at 5°–7° C., and then 19.4 g of triethylamine was added, maintaining the temperature at 5°–8° C. The mixture was allowed to stir at ambient temperature for 16 hrs, and then a solution of 52.4 g of thymol in 38.2 g of triethylamine and 50 mL of dry toluene was added at below 40° C., followed by 0.25 g of 4-dimethylaminopyridine in 40 mL of toluene. The mixture was heated at 80° C. for 2 hrs, cooled to 12° C., and washed with water, aq NaCl, and again with water. The solution of the phosphoramidite was dried by distillation of 200 mL of solvent at reduced pressure between 60° and 70° C. to afford a solution of the product which was of 90–95% purity by gas chromatographic and ³¹P-NMR analysis (δ143 ppm).

B. Bis(2-isopropylphenyl) N,N'-diisopropylphosphoramidite:

To a solution of 15.0 g of 2-isopropylphenol and 10.5 g of triethylamine in 100 mL of hexane was added 60 mL of a solution of N,N-disopropylphosphoramidous dichloride (0.825M in hexane) at ambient temperature over 45 minutes. The mixture was allowed to stir at ambient temperature for at least 16 h, the triethylamine hydrochloride was filtered and washed with two 100-mL portions of hexane, and the combined filtrate and washings were concentrated to provide 19.2 g of the product as an oil. A portion of this (11 g) was crystallized from 20 mL of cold methanol, washed with two 5-mL portions of cold methanol and suction-dried to provide 7.35 g of the pure phosphoramidite as a crystalline solid, mp 35° C. ³¹P-NMR (C₆D₆) δ142.2 ppm; ¹H-NMR (C₆D₆) δ5 1.25 (m, 24H), 3.6 (septet, 2H), 3.9 (m, 2H), 7.0 (m, 4H), 7.2 (m, 4H), and 7.35 (m, 2H).

C. Bis(2-isopropylphenyl)phosphorochloridite:

A solution of 7.21 g of the product from Example 72B in 200 mL of cyclohexane was cooled to 0° C. and anydrous HCl gas was bubbled in over ca. 20 min. Excess HCl was purged by bubbling dry nitrogen through the solution for 10 min. The diisopropylamine hydrochloride was filtered off in a drybox and washed with 50 mL of cyclohexane, and the combined filtrate and washings were concentrated to dryness in vacuo to provide 5.40 g of crude phosphorochloridite as an off, judged to be 90% pure by $^{31}$P-NMR analysis. $^{31}$P-NMR ($C_6D_6$) a 162.4 ppm. Small (5% each) peaks corresponding to triaryl phosphite and diaryl hydrogenphosphonate were present as contaminants, but the chloridite was sufficiently pure to be used for subsequent ligand synthesis.

EXAMPLE 73

Preparation of Bis(2,3-dimethoxyphenyl) phosphorochloridite

In a 250 mL 3-neck flask equipped with condenser, thermometer and addition funnel was charged with 21.547 g of 2,3-dimethoxyphenol, 14.2 g of $NEt_3$, and 140 mg of 4-N,N-dimethylaminopyridine in 35 mL of cyclohexane. 139.8 mL of 0.5M solution of N,N-diisopropyl-dichlorophosphoramidite in hexane was added dropwise over a period of 40 minutes. The mixture was heated to 65° C. for 3.5 hours. The mixture was filtered through silica gel and washed with cyclohexane. The solution was cooled in an ice bath and 140 mL of 1M HCl in ether was added over a period of 45 minutes. The mixture was stirred overnight, filtered, washed with toluene and solvent removed to give 15.98 g of the desired product as a clear pale yellow liquid. $^{31}$P NMR (ppm, $C_6D_6$): 169.9.

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than the foregoing specification, as indicating the scope of the invention.

What is claimed is:

1. A method of making phosphorochloridite comprising contacting a compound of the formula $N(R^{18})_2P(OR^{19})_2$, wherein $R^{18}$ is alkyl and $R^{19}$ is substituted aryl, with gaseous hydrogen chloride to produce $HN(R^{18})_2 \cdot HCl$ and $(R^{19}O)_2PCl$.

2. The method of claim 1 wherein the HCl is not present in excess.

* * * * *